(12) United States Patent
Brown

(10) Patent No.: US 7,869,852 B2
(45) Date of Patent: *Jan. 11, 2011

(54) DIABETES MANAGEMENT SYSTEM

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 151 days.

This patent is subject to a terminal disclaimer.

(21) Appl. No.: 11/925,150

(22) Filed: Oct. 26, 2007

(65) Prior Publication Data

US 2008/0097181 A1 Apr. 24, 2008

Related U.S. Application Data

(60) Continuation of application No. 11/748,031, filed on May 14, 2007, which is a continuation of application No. 11/583,433, filed on Oct. 19, 2006, which is a division of application No. 10/673,045, filed on Sep. 26, 2003, which is a continuation of application No. 09/971,785, filed on Oct. 4, 2001, now abandoned, which is a continuation of application No. 09/119,546, filed on Jul. 20, 1998, now Pat. No. 6,330,426, which is a continuation-in-part of application No. 08/953,883, filed on Oct. 20, 1997, now abandoned, which is a continuation-in-part of application No. 08/757,129, filed on Dec. 3, 1996, now Pat. No. 6,144,837, which is a continuation-in-part of application No. 08/334,643, filed on Nov. 4, 1994, now Pat. No. 5,601,435, said application No. 09/119,546 is a continuation of application No. 08/958,786, filed on Oct. 29, 1997, now Pat. No. 5,913,310, which is a continuation-in-part of application No. 08/857,187, filed on May 15, 1997, now Pat. No. 5,918,603, which is a division of application No. 08/247,716, filed on May 23, 1994, now Pat. No. 5,678,571.

(51) Int. Cl.
*A61B 5/00* (2006.01)

(52) U.S. Cl. ...................................... 600/347; 600/365

(58) Field of Classification Search .................... None
See application file for complete search history.

(56) References Cited

U.S. PATENT DOCUMENTS 3,426,150 A 2/1969 Tygart (Continued)

FOREIGN PATENT DOCUMENTS

EP 0286456 10/1988

(Continued)

OTHER PUBLICATIONS

+5V Powered Isolated RS-232 Drivers/Receivers Maxim Integrated Products.

(Continued)

*Primary Examiner*—Robert L Nasser
(74) *Attorney, Agent, or Firm*—Christopher P. Maiorana, PC

(57) ABSTRACT

A method of diabetes management, comprising (a) providing a remote communications unit in communication with a portable microprocessor-based unit; (b) transmitting blood glucose level data into the portable microprocessor-based unit or the remote unit, or both; (c) running a program of instructions on the portable microprocessor-based unit or on the remote unit, or both, using data corresponding to the blood glucose level data; and (d) providing a signal including instructions to inject insulin when the blood glucose level data indicates.

14 Claims, 19 Drawing Sheets

U.S. PATENT DOCUMENTS

| | | |
|---|---|---|
| 3,566,365 A | 2/1971 | Rawson et al. |
| 3,566,370 A | 2/1971 | Worthington, Jr. et al. |
| 3,581,072 A | 5/1971 | Nymeyer |
| 3,768,014 A | 10/1973 | Smith |
| 3,811,116 A | 5/1974 | Takeuchi et al. |
| 3,883,235 A | 5/1975 | Lynn et al. |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A * | 3/1988 | Allen, III .................. 600/300 |
| 4,738,451 A | 4/1988 | Logg |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |
| 4,799,156 A | 1/1989 | Shavit et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,916,441 A | 4/1990 | Gombrich |
| 4,931,934 A | 6/1990 | Snyder |
| 4,933,873 A * | 6/1990 | Kaufman et al. ............ 704/270 |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A * | 5/1991 | Beckers ...................... 600/316 |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,108,889 A * | 4/1992 | Smith et al. .................... 435/4 |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,552 A | 7/1992 | Fang et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips et al. |

| | | | | | |
|---|---|---|---|---|---|
| 5,307,263 A | 4/1994 | Brown | 5,613,495 A | 3/1997 | Mills et al. |
| 5,309,919 A | 5/1994 | Snell et al. | 5,619,991 A | 4/1997 | Sloane |
| 5,321,009 A | 6/1994 | Baeder et al. | 5,624,265 A | 4/1997 | Redford et al. |
| 5,325,288 A | 6/1994 | Satou | 5,628,309 A | 5/1997 | Brown |
| 5,329,459 A | 7/1994 | Kaufman et al. | 5,629,981 A | 5/1997 | Nerlikar |
| 5,329,608 A | 7/1994 | Bocchieri et al. | 5,631,844 A | 5/1997 | Margrey et al. |
| 5,331,549 A | 7/1994 | Crawford, Jr. | 5,633,910 A | 5/1997 | Cohen |
| 5,333,981 A | 8/1994 | Pronovost et al. | 5,635,532 A | 6/1997 | Samid |
| 5,335,338 A | 8/1994 | Proesel | 5,640,569 A | 6/1997 | Miller et al. |
| 5,339,821 A | 8/1994 | Fujimoto | 5,640,953 A | 6/1997 | Bishop et al. |
| 5,341,291 A | 8/1994 | Roizen et al. | 5,642,731 A | 7/1997 | Kehr |
| 5,343,239 A | 8/1994 | Lappington et al. | 5,642,936 A | 7/1997 | Evans |
| 5,344,324 A | 9/1994 | O'Donnell et al. | 5,651,363 A | 7/1997 | Kaufman et al. |
| 5,357,427 A | 10/1994 | Langen et al. | 5,651,775 A | 7/1997 | Walker et al. |
| 5,366,896 A | 11/1994 | Margrey et al. | 5,659,691 A | 8/1997 | Durward et al. |
| 5,368,562 A | 11/1994 | Blomquist et al. | 5,666,487 A | 9/1997 | Goodman et al. |
| 5,371,687 A | 12/1994 | Holmes, II et al. | 5,670,711 A | 9/1997 | Detournay et al. |
| 5,375,604 A | 12/1994 | Kelly et al. | 5,675,635 A | 10/1997 | Vos et al. |
| 5,377,100 A | 12/1994 | Pope et al. | 5,678,562 A | 10/1997 | Sellers |
| 5,390,238 A | 2/1995 | Kirk et al. | 5,678,571 A | 10/1997 | Brown |
| 5,399,821 A | 3/1995 | Inagaki et al. | 5,679,075 A | 10/1997 | Forrest et al. |
| 5,410,471 A | 4/1995 | Alyfuku et al. | 5,680,590 A | 10/1997 | Parti |
| 5,410,474 A | 4/1995 | Fox | 5,680,866 A | 10/1997 | Kangas et al. |
| 5,429,140 A | 7/1995 | Burdea et al. | 5,687,322 A | 11/1997 | Deaton et al. |
| 5,431,690 A | 7/1995 | Schaldach et al. | 5,687,717 A | 11/1997 | Halpern et al. |
| 5,431,691 A | 7/1995 | Snell et al. | 5,687,734 A | 11/1997 | Dempsey et al. |
| 5,434,611 A | 7/1995 | Tamura | 5,689,652 A | 11/1997 | Lupien et al. |
| 5,438,607 A | 8/1995 | Przygoda, Jr. et al. | 5,692,906 A | 12/1997 | Corder |
| 5,438,983 A | 8/1995 | Falcon | 5,704,364 A | 1/1998 | Saltzstein et al. |
| 5,441,047 A | 8/1995 | David et al. | 5,704,366 A | 1/1998 | Tacklind et al. |
| 5,449,334 A | 9/1995 | Kingsbury | 5,704,902 A | 1/1998 | Vandenbelt et al. |
| 5,454,721 A | 10/1995 | Kuch | 5,704,922 A | 1/1998 | Brown |
| 5,454,722 A | 10/1995 | Holland et al. | 5,710,178 A | 1/1998 | Samid |
| 5,456,606 A | 10/1995 | McIntyre | 5,710,918 A | 1/1998 | Lagarde et al. |
| 5,456,692 A | 10/1995 | Smith, Jr. et al. | 5,711,297 A | 1/1998 | Iliff |
| 5,458,123 A | 10/1995 | Unger | 5,714,319 A | 2/1998 | Joutel et al. |
| 5,467,269 A | 11/1995 | Flaten | 5,715,451 A | 2/1998 | Marlin |
| 5,471,039 A | 11/1995 | Irwin, Jr. et al. | 5,715,823 A | 2/1998 | Wood et al. |
| 5,471,382 A | 11/1995 | Tallman et al. | 5,717,739 A | 2/1998 | Dyer et al. |
| 5,483,276 A | 1/1996 | Brooks et al. | 5,717,913 A | 2/1998 | Driscoll |
| 5,488,412 A | 1/1996 | Majeti et al. | 5,720,733 A | 2/1998 | Brown |
| 5,488,423 A | 1/1996 | Walkingshaw et al. | 5,722,418 A | 3/1998 | Bro |
| 5,501,231 A | 3/1996 | Kaish | 5,727,153 A | 3/1998 | Powell |
| 5,502,636 A | 3/1996 | Clarke | 5,730,124 A | 3/1998 | Yamauchi |
| 5,502,726 A | 3/1996 | Fischer | 5,730,654 A | 3/1998 | Brown |
| 5,504,519 A | 4/1996 | Remillard | 5,732,696 A | 3/1998 | Rapoport et al. |
| 5,517,405 A | 5/1996 | McAndrew et al. | 5,732,709 A | 3/1998 | Tacklind et al. |
| 5,518,001 A | 5/1996 | Snell | 5,734,413 A | 3/1998 | Lappington et al. |
| 5,519,058 A | 5/1996 | Gonick et al. | 5,749,083 A | 5/1998 | Koda et al. |
| 5,519,433 A | 5/1996 | Lappington et al. | 5,752,234 A | 5/1998 | Withers |
| 5,523,232 A | 6/1996 | Sechler | 5,754,740 A | 5/1998 | Fukuoka et al. |
| 5,536,249 A | 7/1996 | Castellano et al. | 5,760,771 A | 6/1998 | Blonder et al. |
| 5,542,420 A | 8/1996 | Goldman et al. | 5,772,585 A | 6/1998 | Lavin et al. |
| 5,544,649 A | 8/1996 | David et al. | 5,778,882 A | 7/1998 | Raymond et al. |
| 5,546,943 A | 8/1996 | Gould | 5,782,814 A | 7/1998 | Brown et al. |
| 5,549,117 A | 8/1996 | Tacklind et al. | 5,785,650 A | 7/1998 | Akasaka et al. |
| 5,550,575 A | 8/1996 | West et al. | 5,787,295 A | 7/1998 | Nakao |
| 5,553,609 A | 9/1996 | Chen et al. | 5,791,342 A | 8/1998 | Woodard |
| 5,558,638 A | 9/1996 | Evers et al. | 5,792,117 A | 8/1998 | Brown |
| 5,564,429 A | 10/1996 | Bornn et al. | 5,793,969 A | 8/1998 | Kamentsky et al. |
| 5,569,212 A | 10/1996 | Brown | 5,794,219 A | 8/1998 | Brown |
| 5,572,421 A | 11/1996 | Altman et al. | 5,794,251 A | 8/1998 | Watanabe et al. |
| 5,572,646 A | 11/1996 | Kawai et al. | 5,796,393 A | 8/1998 | MacNaughton et al. |
| 5,574,828 A | 11/1996 | Hayward et al. | 5,799,318 A | 8/1998 | Cardinal et al. |
| 5,576,952 A | 11/1996 | Stutman et al. | 5,800,458 A | 9/1998 | Wingrove |
| 5,583,758 A | 12/1996 | McIlroy et al. | 5,802,494 A | 9/1998 | Kuno |
| 5,590,648 A | 1/1997 | Mitchell et al. | 5,802,534 A | 9/1998 | Hatayama et al. |
| 5,593,349 A | 1/1997 | Miguel et al. | 5,806,057 A | 9/1998 | Gormley et al. |
| 5,593,390 A | 1/1997 | Castellano et al. | 5,810,747 A | 9/1998 | Brudny et al. |
| 5,594,637 A | 1/1997 | Eisenberg et al. | 5,819,735 A | 10/1998 | Mansfield et al. |
| 5,596,994 A | 1/1997 | Bro | 5,822,544 A | 10/1998 | Chaco et al. |
| 5,597,307 A | 1/1997 | Redford et al. | 5,822,715 A | 10/1998 | Worthington et al. |
| 5,601,435 A | 2/1997 | Quy | 5,825,283 A | 10/1998 | Camhi |

| | | |
|---|---|---|
| 5,827,180 A | 10/1998 | Goodman |
| 5,828,943 A | 10/1998 | Brown |
| 5,832,448 A | 11/1998 | Brown |
| 5,835,896 A | 11/1998 | Fisher et al. |
| 5,840,020 A | 11/1998 | Heinonen et al. |
| 5,842,976 A | 12/1998 | Williamson |
| 5,868,669 A | 2/1999 | Iliff |
| 5,868,683 A | 2/1999 | Protopapas et al. |
| 5,875,432 A | 2/1999 | Sehr |
| 5,879,163 A | 3/1999 | Brown et al. |
| 5,882,338 A | 3/1999 | Gray |
| 5,887,133 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hofbert et al. |
| 5,933,136 A | 8/1999 | Brown |
| 5,935,060 A | 8/1999 | Iliff |
| 5,940,801 A | 8/1999 | Brown |
| 5,941,829 A | 8/1999 | Saltzstein et al. |
| 5,945,651 A | 8/1999 | Chorosinski et al. |
| 5,951,300 A | 9/1999 | Brown |
| 5,954,641 A | 9/1999 | Kehr et al. |
| 5,956,501 A | 9/1999 | Brown |
| 5,960,403 A | 9/1999 | Brown |
| 5,961,446 A | 10/1999 | Beller et al. |
| 5,966,526 A | 10/1999 | Yokoi |
| 5,971,855 A | 10/1999 | Ng |
| 5,971,922 A | 10/1999 | Arita et al. |
| 5,983,003 A | 11/1999 | Lection et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 5,997,502 A | 12/1999 | Reilly et al. |
| 6,001,065 A | 12/1999 | DeVito |
| 6,022,315 A | 2/2000 | Iliff |
| 6,022,615 A | 2/2000 | Rettenbacher |
| 6,023,686 A | 2/2000 | Brown |
| 6,024,281 A | 2/2000 | Shepley |
| 6,029,138 A | 2/2000 | Khorasani et al. |
| 6,032,119 A | 2/2000 | Brown et al. |
| 6,035,328 A | 3/2000 | Soukal |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,068,615 A | 5/2000 | Brown et al. |
| 6,095,985 A | 8/2000 | Raymond et al. |
| 6,101,478 A | 8/2000 | Brown |
| 6,110,148 A | 8/2000 | Brown et al. |
| 6,113,578 A | 9/2000 | Brown |
| 6,138,145 A | 10/2000 | Kawanaka |
| 6,144,837 A | 11/2000 | Quy |
| 6,151,586 A | 11/2000 | Brown |
| 6,161,095 A | 12/2000 | Brown |
| 6,167,362 A | 12/2000 | Brown et al. |
| 6,167,386 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| D439,242 S | 3/2001 | Brown et al. |
| 6,210,272 B1 | 4/2001 | Brown |
| 6,221,012 B1 | 4/2001 | Maschke et al. |
| 6,233,539 B1 | 5/2001 | Brown |
| 6,240,393 B1 | 5/2001 | Brown |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,334,778 B1 | 1/2002 | Brown |
| 6,352,523 B1 | 3/2002 | Brown et al. |
| 6,368,273 B1 | 4/2002 | Brown |
| 6,370,513 B1 | 4/2002 | Kolawa et al. |
| 6,375,469 B1 | 4/2002 | Brown |
| 6,379,301 B1 | 4/2002 | Worthington et al. |
| 6,381,577 B1 | 4/2002 | Brown |
| 6,436,036 B1 | 8/2002 | Miller-Kovach et al. |
| 6,513,532 B2 | 2/2003 | Mault et al. |
| 2002/0019748 A1 | 2/2002 | Brown |
| 2004/0106855 A1 | 6/2004 | Brown |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |

FOREIGN PATENT DOCUMENTS

| | | |
|---|---|---|
| EP | 0320749 | 6/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 5/1995 |
| EP | 676709 | 10/1995 |
| EP | 680727 | 11/1995 |
| EP | 761160 | 3/1997 |
| EP | 08131551 | 12/1997 |
| EP | 0251520 | 1/1998 |
| GB | 2218831 | 11/1989 |
| GB | 2225637 | 6/1990 |
| JP | 54005785 | 1/1979 |
| JP | 54146633 | 11/1979 |
| JP | 62226278 | 10/1987 |
| JP | 5155024 | 6/1993 |
| JP | 5266002 | 10/1993 |
| JP | 1995407095963 | 4/1995 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9831275 | 7/1998 |
| WO | WO-9839933 | 9/1998 |

OTHER PUBLICATIONS

Adilman; "Videogames: Knowing the Score"; Creative Computing; v9; p. 224(5); Dec. 1983; Dialog: File 148, Acc# 01891055.

AdOptimizer—Ad Management Software for Websites, Newsbytes, pNEW10040041, Oct. 4, 1996.

Albisser, A.M. "Intelligent Instrumentation in Diabetic Management", CRC Critical Reviews in Biomedical Engineering, vol. 17, No. 1, pp. 1-24.

Anonymous, "Health Hero Network, Inc. Receives First-Ever FDA Clearance for Connecting Medical Devices to Internet", PR Newswire, (Dec. 2, 1993), 3 pages.

Antique Collector, Putting the Lot on the Net, vol. 66, Issue 9, p. 26, Downloaded from Corporate Resource Net, Nov./Dec. 1995.

Bai, "Design of home healthcare network", IEEE 1997 pp. 1657-1658.

Billiard, A., et al. "Telematic Transmission of Computerized Blood Glucose Profiles for IDDm Patients", Diabetes Care, (Feb. 1991), vol. 14, No. 2, pp. 130-134.

Blood Glucose Monitors, Portable Health Device, (1998), vol. 17(9), pp. 253-271.

Bower, "Brain Clues to Energy-efficient Learning", Science News, (Apr. 1992), v. 141; p215(1); Dialog: File 647, Acct# 12123949.

Brenman et al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996; Ref: XP-002104701.

Bruce, "Health Hero Network CEO, CNNfn", Digital Jam, (Dec. 1, 1999), 3.

Bruce, et al., "The Effects of Sympathetic Nervous System Activation and Psychological Stress . . . "; Diabetologia; 35(9); 1992; 835-843; Dialog: File 5, Acc#9629427. (9 pages).

Brunetti, P., et al., "A Simulation Study on a Self-Turning Portable Controller of Blood Glucose", The International Journal of Artificial Organs, (1993), vol. 16, No. 16, pp. 51-57.

Caprihan, A., et al., "A Simple Microcomputer for Biomedical Signal Processing", IECI '78 Annual Conference Proceedings on Industrial Applications of Microprocessors, (Mar. 20, 1978), 18-23.

Cathay Pacific Airways-USA receives more than 1,300 bids during first five days of CyberAuction; Business Wire, Oct. 18, 1995, p10181119.

Cathay Pacific Airways-USA to Hold First-Ever Internet CyberAuction; CyberTravelers Can Bid for 50 Business Class Round Trips to Hong Kong—No Minimum Bid; Business Wire; p9261084; Sep. 26, 1995; DIALOG: File 148, Acc#08167091.

CD-ROM Mavericks: Proprietary TV-Based Players, Byte Guide to CD-ROM, pp. 100-105.

Central Fetal Monitoring Systems with Optical Disk Storage, New Technology Brief, (Nov./Dec. 1998), vol. 2, No. 6, pp. 249-251.

Cheng, Joe H., "PCT Search Report", (Jan. 11, 1996).

DigiPet Instruction Manual, 1997.

Digital Doggie; retrieved from URL http://www.virtualpet.com/vp/farm/gigapet/ddoggie.htm Apr. 23, 2000.

Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.

Edelson; "Fashion Reevaluates Flickering Fortunes of TV Home Shopping"; WWD; v170 n87; p1(3); Nov. 8, 1995; DIALOG: File 148, Acc#08289119.

EP European Search Report, From 6858P005EP, (Mar. 27, 1998).

Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.

Finston, "Parent + Teacher = Healthy Child", Diabetes Forecast, (Apr. 1994), v47 n9; P26(5); Dialog: file 149, Acc# 15804228.

Fox, "Not My Type: Type B Behavior, Type I Diabetes Plus Stress Equals Blood Sugar Blues", Health, (Mar. 1998), v20 n3; pp22(1); Dialog: File 149, Acc# 06397959.

Franklin; "Proposed Auction Rules for PCS: The FCC Plans to Use Competitive Bidding, but Exact Procedures are Undefined"; Cellular Business; v10 n13; p. 18(2); Dec. 1993; DIALOG: File 148, Acc#06787310.

Frieberger, Paul, "Video Game Takes on Diabetes Superhero 'Captain Novolin' Offers Treatment Tips", San Francisco Examiner, (Jun. 26, 1992), Fourth Edition, Business Section B1.

Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.

Future of the Virtual Pet Industry, 1997 [retrieved on Apr. 23, 2000], Retrieved from <URL:www.virtualpet.com/vp/ future/future.htm>.

Gardner, et al.; "Comprehension and Appreciation of Humorous Material Following Brain Damage"; Brain; Sep. 1975; 98(3); pp. 399-412; Dialog: File 153, Acc#02859983. (14 pages).

Gauntlet (for PC) rulebook by Mindscape Inc. (Gauntlet by Apple);1985.

Giga Farm; retrieved from URL http://www.virtualpet.com/vp/farm/gigapet/gpfarm/gpfarm.htm Apr. 23, 2000.

Giga Pets, 1997 [retrieved on Apr. 23, 2000], Retrieved from <URL:www.virtualpet.com/vp/farm/gigapet/gigapet.htm>.

Gordon; "Auctions Become High Tech"; Dealer Business; v29 n7; p. 21(4); Mar. 1995; DIALOG: File 148, Acc#07862519.

Guiffrida, et al., Should We Pay the Patient? Review of Financial Incentives to enhance Patient Compliance:, Biomedical Journal, (1997), vol. 315, pp. 703-707.

Hauben, Jay R., "A Brief History of the Cleveland Free-Net", available at http://www.ais.org/~irh/acn7-1.a09.html, (1995) pp. 1-4.

Hauser, et al., "Will Computers Replace or Complement the Diabetes Educator?", The Medical Journal of Australia, (Oct. 5, 1992), vol. 157, 489-491.

Horio, Hiroyuki, et al., "Clinical Telecommunication Network System for Home Monitoring", Medical & Biological Engineering & Computing, (Mar. 1994), vol. 32, 227-230.

How Flash Memory Works, Internet printout of URL address: http://www.howstuffworks.com/flash-memory4.htm, (Sep. 28, 2002), 2 pages.

Howey, et al., "A Rapidly Absorbed Analogue of Human Insulin"; Diabetes, vol. 43, Mar. 1994, pp. 396-402. (7 pages).

Hunter, "Technological Advances in Bedside Monitoring: Biosensors", Archives and Laboratory Medicine, (Jul. 1987), pp. 633-636.

Hutheesing, Nikhil, "An on-line gamble", Forbes, v157 n10 p. 288(1), May 20, 1996.

Introducing the Next Generation of About Your Diabetes, U.S. Pharmacopical Convention and American Diabetes Association, (1993).

Jaffrey et al.; "PIN: An Associated Protein Inhibitor of Neuronal Nitric Oxide Synthase"; Science; vol. 274; Nov. 1, 1996; Ref: XP 002050141.

Jimison et al., "Patient-Specific explanation in models of chronic disease", Revised Feb. 1992 Artificial Intelligence in Medicine 4 (1992) 191-205.

Jones, Chris, "Microsoft readies DocObject; technology will allow document editing in Web browsers", InfoWorld, v18 n18 p. 48(1), Apr. 29, 1996.

Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.

Kaufman, Steven, B., "The Learning Game", Nation's Business, (Nov. 1993).

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.

Lachnit, Carroll, "Hawkin's Online Auction", Photo District News, vol. 16, Issue 1, p. 18, Jan. 1996.

Lacyk, John, "PCT Search Report", (Jun. 12, 1997).

Latman, N. S., "Evaluation of Electronic, Digital Blood Glucose Monitors", Biomedical Instrumentation and Technology, (1991), vol. 25, No. 1, 43-49.

Leyerle, Beverly J., et al., "The PDMS as a Focal Point for Distributed Patient Data", International Journal of Clinical Monitoring and Computing, (1988), vol. 5, pp. 155-161.

Luebke, Cathy, "Barrett-Jackson Auction Turns High-Tech", Business Journal, vol. 16, Issue 12, pp. 11, Jan. 19, 1996.

Makikawa, M., et al., "Microprocessor-Based Memory Device for Ambulatory Heart Rate and Physical Activity Recording", Methods of Information in Medicine, (1994), vol. 33, No. 1, pp. 94-96.

Marsh, David G. "Approaches Toward the Genetic Analysis of Complex Traits Asthma and Atrophy", Am. J. Respir.Crit.Care Med., (1997), vol. 156, pp. S-133-S138.

Martinez, Fernando D., "Complexities of the Genetics of Asthma", Am.J. Respir. Crit. Care Med., (1997), vol. 156, pp. S117-S122.

Marx, Wendy, "More than just the Scores: ESPNET SportsZone is a model for expanding brand names online", InformationWeek, n576 p. 61(2), Apr. 22, 1996.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

McCullagh, PJ et al., "Computerized paradigms for eliciting the contingent negative variation event-related potential," Proceedings of the Annual International Conference of the Engineering in Medicine & Biology Society, IEEE, Conf. 14, p2481-2483, Oct. 1992.

Meissner, et al., "Building an Integrated Clinical and Research Network", Proceedings of the SPIE, (Oct. 24, 1995), vol. 2618, p. 92-99.

Miles, Laughton E., "A Portable Microcomputer for Long-Term Physiological Monitoring in the Home and Work Environment", Medical Monitoring in the Home and Work Environment, (1990), pp. 47-57.

Mims; "Psychological Testing"; Computers & Electronics; v23; p. 22(6); Feb. 1985; Dialog: File 47, Acc# 2654858.

Moore, "New Applications Break Through Storage Boundaries", Computer Technology Review, (Oct. 1999), vol. 19, No. 10 p. 1.

Mule. rulebook by Electronic Arts, 1983.

Nano Baby Instructions; retrieved from file://C:\My Documents\Nano Baby Instructions.htm Apr. 23, 2000.

Nano Fighter Pets; retrieved from URL http://www.virtualpet.com/vp/farm/nano/nfighter.htm Apr. 23, 2000.

Nano Page, 1997 [retrieved on Apr. 23, 2000], Retrieved from <URL:www.virtualpet.com/vp/farm/nano/nano.htm>.

Octhigotchi Instruction Manual, 1997. Dino-Kun Instruction Manual, 1997.

O'Donnell; "Alan's At It Again"; Bond Buyer; v309 n29448; p. 1(3); Jul. 21, 1994; DIALOG: File 148, Acc#07478152.

Onsale Joins Fray as Online Shopping Picks Up Speed: INTERNET BOOMS; Computer Reseller News; Jun. 5, 1995; p. 73; DIALOG: File 16, Acc#05649796.

ONSALE Onsale Brings Thrill of Auctions and Bargain Hunting Online; Unique Internet retail service debuts with week-long charity auction for The Computer Museum in Boston, May 24, 1995; Dialog Abstract: File 610, Acc#0489267.

Pfeiffer, E. F., "The Glucose Sensor: The Missing Link in Diabetes Therapy", Hormone and Metabolic Research, (1990), vol. 24m Suppl. pp. 154-164.

Playmates Toys deals knockout blow to virtual pet competitors with introduction of Nano Fighter™ for Boys; New Nano Pet Fighting Pet Press Release; retrieved from URL http://www.virtualpet.com/vp/farm/nano/nfightpr.htm Apr. 23, 2000.

Playmates Toys leads Americas virtual pet craze into its next generation by introducting talking Nano Pals; Talking Nano Pet Press Release; Nov. 18, 1997; retrieved from URL http://www.virtualpet.com/vp/farm/nano/talkn/tnpress.htm on Apr. 23, 2000.

Poitout, V., et al. "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Polson, Gary "Recent Developments and Trends in Keychain Virtual Pets," 1997 [retrieved on Apr. 23, 2000], Retrieved from <URL:www.virtualpet.com/vp/future/trends1a.htm>.

Potter, David, "Fundamentals of PC-Based Data Acquisition", SENSORS, (Feb. 1994), pp. 12-20.

Reis, H, "Telemedicine: Transmitting Expertise to the Point of Care Toward an Electronic Patient Record"; '97, Nashville, TN, Apr. 27-May 3, 1997, pp. 248-256, v. 3.

Research project launched to improve health of America's communities; new Disney community in Florida is focus of program. Business Wire, p10011142. Oct. 1, 1996.

Results of the world's first on-line auction, http://www.christies.com.

RO_AUCTION Auctioneers Property Database System and RO_AUCTION Auctioneers Accounting System; RO-AUCTION features; Dec. 4, 1995.

Roberts; "Diabetes and Stress: A Type A Connection?", Psychology Today, (Jul. 1987), v. 21; pp22(1); Dialog: File 149, Acc# 05038381.

Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.

Save the earth artrock auction, http://www.commerce.com.saveearth. Auction Web, http://www.ebay.com.

Schement, "An Intelligent Controller for Neurophysiological Experiments," Proceeding of the Annual Symposium on Computer Based Medical Systems, Durham, Jun. 14-17, 1992, p. 528, line 1—p. 529, line 21.

Schenkels, P., "Supplementary European Search Report", Application No. EP 97 92 2716, (Mar. 11, 2002).

Schork, Nicholas J., "Genetics of Complex Disease", Am.J.Respir. Crit. Care Me., (1997), vol. 156, pp. S103-S109.

Schrezenmeir, J. et al., "Computer Assisted Insulin Dosage Adjustment—Perspective for Diabetes Control", Hormone and Metabolic Research, Supplement Series, (1990), vol. 24, pp. 116-123.

Seigmann;"Nowhere to Go but Up"; PC Week; v12 n42, p. A5(1); Oct. 23, 1995; DIALOG: File 148, Acc#08222496.

Seybold—New Horizons teams with Duke, Real Media; The Seybold Report on Desktop Publishing, v10 n12 p. 24(1), Aug. 12, 1996.

Shandle, Jack, "Who Will Dominate The Desktop in the 90's?", , Electronics, Feb. 1990, pp. 48-50. (3 pages) Cited by 2 patents.

Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.

Skolnick et al. "Simultaneous Analysis of Multiple Polymorphic Loci Using Amplified Sequence Polymorphisms (ASPs)"; Genomics. 2: 273-279.

Soeldner, J. S., "Treatment of Diabetes Mellitus by Devices", The American Journal of Medicine, (Jan. 1981), vol. 70, 183-194.

Spitzer et al.; "The moderating effect of age on self-care"; Western Journal Of Nursing Research, v18, n2, p136(13), Apr. 1996.

Symbol Technologies; "Healthcare Mobility Solutions for the PPT8800", Feb., 2004.

Talking Nano Puppy; retrieved from URL http://www.virtualpet.com/vp/farm/nano/talkn/talkn.htm Apr. 23, 2000.

Tamagotchi, 1997 [retrieved on Apr. 23, 2000], Retrieved from <URL:www.virtualpet.com/vp/farm/lleg/Ileg.htm>.

Tandy Radio Shack , "The description of the Tandy Radio Shack TRS-80 Model 100/102 device available at http://www.old-computuers.com/musuem/computer.asp?c=233", World Wide Web, (Feb. 13, 2004), 1-3.

Telemedicine Provides Two-Way Computer Link for Parents of Very Premature Infants. PR Newswire. p1007NEM034. Oct. 7, 1996.

Theme Hospital, product review 1996 [retrieved Apr. 21, 2000], Retrieved from <URL:www.vigilante.co.uk/ep/misc/hospital.htm>.

Towards a partnership of care, M2 Presswire, Jun. 14, 2000.

United Healthcare's OPTUM Division goes online to better health by announcing a unique internet application. PR Newswire, p0801MNTH004. Aug. 1, 1996.

Updike, Stuart J., et al., "Laboratory Evaluation of New Reusable Blood Glucose Sensor", Diabetes Care, (Nov./Dec. 1998), vol. 11, No. 10, pp. 801-807.

Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.

Vallera, D. A., et al., "Accuracy of Portable Blood Glucose Monitoring", American Journal of Clinical Pathology, (1991), vol. 95, No. 2, pp. 247-252.

Virtual Pet Product Reviews, 1997 [retrieved on Apr. 23, 2000], Retrieved from <URL:www.virtualpet.com/vp/farm/reviews/reviews,htm>.

Virtual Tomagutchi, 1998 [retrieved Apr. 23, 2000], Retrieved from <URL:www.sttf.org/english/action/tomagutchi.html>.

Voelker, Rebecca, "Shoe Leather Therapy is Gaining on TB", Jama, (Mar. 13, 1996), vol. 275, 743.

Wilkins, Aaron. "Expanding Internet access for health care consumers", Health Care Management Review, Summer, Jul. 1999, 24-30.

Wyatt, J. C., "Clinical Data Systems, Part 2: Components and Techniques", Lancet, (Dec. 1994), vol. 344, No. 8937, pp. 1609-1614.

Yoshizawa, Daisuke, et al., "The Development of a Data Processing System with Personal Computer MSX Standard System for Flow Injection Analysis", Journal of Flow Injection Analysis, (1988), v.5, No. 2, pp. 101-110.

Thompson and Vandenberg, Clinical Biochemistry (1986) 19:255-261.

Velho et. al., Biomed. Biochim. Acta (1989) 48(11/12):957:964.

Complaint filed August 17, 2006, *Abbott Diabetes Care Inc.* v. *Decom, Inc.*

* cited by examiner

PROGRAM ASSIGNMENT SCREEN

AVAILABLE PROGRAMS:     STUDENTS:

166 — [X] DIABETES AND EXERCISE      168 — [X] DAN LINDSEY
     [ ] FOOD EXCHANGES AND DIET     178   [ ] MARK SMITH
176  [ ] BLOOD GLUCOSE MONITORING         [ ] DEAN JONES

[ ADD NEW PROGRAM ] [ SAVE NEW LISTING ] [ ADD NEW PATIENT ] — 174

170 — [ ASSIGN PROGRAM ]    [ DELETE PROGRAM ] — 172

*FIG. 3*

REPORT SCREEN

| STUDENT | ASSIGNED PROGRAM | PROGRAM COMPLETED | RESULTS/SCORE |
|---|---|---|---|
| DAN LINDSEY | DIABETES AND EXERCISE | MAY 1, 1997. 5:22 PM | COMPLETED |
| MARK SMITH | FOOD EXCHANGES AND DIET | MAY 3, 1997 3:54 PM | 79 |
| DEAN JONES | BLOOD GLUCOSE MONITORING | NOT COMPLETED | N/A |

*FIG. 4*

Thank you for watching "Living With Diabetes", brought to you by Acme Pharmaceuticals. Please answer the following questions by pushing the numbered button on your remote control which corresponds to the best answer.

A. Do you visit your doctor regularly?
    1 - yes    2 - sometimes    3 - no

B. Do you monitor your sugar (glucose) intake?
    1 - yes    2 - sometimes    3 - no C. Do you exercise regularly?
    1 - yes    2 - sometimes    3 - no

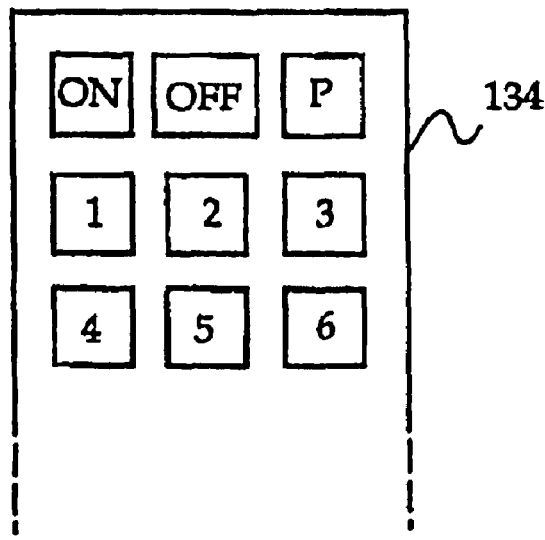

*FIG. 5*

DIABETES MANAGEMENT SYSTEM

RELATED APPLICATIONS

This application is a Continuation of application Ser. No. 11/748,031, filed May 14, 2007, which is a Continuation of application Ser. No. 11/583,433, filed Oct. 19, 2006, which is a Divisional of application Ser. No. 10/673,045, filed Sep. 26, 2003, which is a Continuation of application Ser. No. 09/971,785, filed Oct. 4, 2001, now abandoned, which is a Continuation of application Ser. No. 09/119,546 filed Jul. 20, 1998, now U.S. Pat. No. 6,330,426, which is a Continuation-In-Part of application Ser. No. 08/953,883 filed Oct. 20, 1997, now abandoned, which is a Continuation-In-Part of application Ser. No. 08/757,129 filed Dec. 3, 1996, now U.S. Pat. No. 6,144,837, which is a Continuation-In-Part of U.S. application Ser. No. 08/334,643, filed on Nov. 4, 1994, now U.S. Pat. No. 5,601,435; and the application Ser. No. 09/119,546 filed Jul. 20, 1998, now U.S. Pat. No. 6,330,426, is also a Continuation of application Ser. No. 08/958,786, filed Oct. 29, 1997, now U.S. Pat. No. 5,913,310, which is a Continuation-In-Part of application Ser. No. 08/857,187, filed May 15, 1997, now U.S. Pat. No. 5,918,603, which is a Divisional of application Ser. No. 08/247,716, filed May 23, 1994, now U.S. Pat. No. 5,678,571. All of the above applications are hereby incorporated by reference.

FIELD OF THE INVENTION

The present invention relates to the field of medical treatment, and in particular to the treatment of medical conditions in human patients.

BACKGROUND OF THE INVENTION

One of the biggest problems many healthcare providers face is their patients' lack of knowledge. Patients may lack knowledge on basic preventative measures, such as why they should exercise, eat right, and not smoke. Patients may also lack knowledge on conditions or diseases they do have, such as how to measure their blood glucose levels if they are diabetic. This lack of knowledge is a problem for healthcare providers because patients who do not know how to take care of themselves are ill more frequently. Thus, they must visit their doctors more often, sometimes incurring additional costs for hospital stays or laboratory tests. This results in greater fees for the patient, his or her insurance company, and often the taxpayers.

An example of this problem is seen in some diabetes patients. Diabetic patients must regularly receive insulin shots and adhere to a specific diet in order to control their blood glucose levels. Unfortunately, some diabetic patients do not understand all the reasons why they should have regular insulin shots or why they should or should not eat certain foods. In addition, many diabetic patients are unaware of the health consequences should they not follow their treatment plan. As a result, such patients are sicker and require more healthcare than those patients who understand all aspects of their diseases. Sicker patients require more healthcare, which is expensive and time-consuming for healthcare professionals, insurance companies, and the patients themselves.

One way this problem is handled is by increasing the amount of education patients receive about their lifestyle choices and/or their diseases. When patients know what they need to do to stay healthy, they are less inclined to visit their doctors as frequently. In addition, if patients understand the health problems that will result from not taking care of themselves, they will be more likely to follow their prescribed treatments.

Educational forms range from pamphlets in a doctor's office to radio announcements to television shows. Paper-based educational material is cheap, easy to produce, and easy to distribute. Unfortunately, pamphlets or articles are limited to words and pictures and are usually quite boring, which makes it unlikely that patients will enjoy and remember reading them. Radio announcements and television shows are more lively and entertaining, but they are broadcast to the general public. Thus they cannot be customized to a particular patient.

Due to technological advances, patients can now be educated using CD-ROMs, the Internet, and multimedia processors. U.S. Pat. No. 5,307,263 by the present inventor discloses a modular, microprocessor-based health monitoring system. The hand-held unit has a display screen, a control button pad, interchangeable program cartridges, and sensors for monitoring a variety of healthcare data. The program cartridges include motivational and educational material related to use of the device, including step-by-step instructions. Acquired data may be transmitted to a data management unit via an interface cable, or to a clearing house via telephone lines. A program cartridge for monitoring glucose levels and a glucose sensor is disclosed for the purpose of caring for children with diabetes.

U.S. Pat. Nos. 5,597,307 and 5,624,265 by Redford and Stern describe an educational system and apparatus aimed at children which also uses a multimedia processor. This invention comprises a remote control located in a book or other printed publication. A child can read the book while watching the display generated by the multimedia processor, and then press the buttons in the remote control book to alter what he sees.

None of the above education systems allow an individual to automatically access assigned educational programs remotely. The inventions described above provide general educational programs which are not tailored to any one individual. Neither system provides confirmation that an individual has completed the educational program. Neither system allows a healthcare provider nor teacher to easily custom-design which educational programs a patient or individual is to view. Finally, neither system provides a patient or individual access to an unlimited number of educational programs.

Medical conditions associated with a patient's behavior pattern or well-being are typically evaluated and treated in therapy sessions conducted by a physician or a health care specialist. Depending on the ailment, a preliminary picture of the patient's condition may be available to the specialist in the form of answers to questionnaires or results of a battery of tests. This applies to psychological conditions such as schizophrenia, depression, hyperactivity, phobias, panic attacks, anxiety, overeating, and other psychological disorders. In fact, the number of diagnostic tests presently available for classifying these conditions is vast. Such tests rely on the patient to perform a self-examination and to respond candidly to a series of personal questions. Since most tests differ in their basic scientific assumptions the results obtained are not standardized and can not often be used to make meaningful case comparisons.

Consequently, the above-mentioned psychological conditions are fully diagnosed and treated in therapy sessions. In these settings the specialist can better evaluate the state of his patient and design appropriate, individualized treatment.

Unfortunately, because of the amount of time required to do this, diagnosis and treatment are very expensive.

The actual therapeutic changes in the patient occur outside of therapy as the patient applies cognitive and behavioral strategies learned in therapy to problem encountered in day-to-day situations. Progress is predicated to a large extent on patient cooperation, discipline, and self-management. Diaries are employed to ensure patient compliance. Still, in many instances, lack of compliance to long-term therapy regimes presents a major obstacle to successful treatment. Children are a particularly difficult group of patients in this respect. Frequently, they lack the understanding, maturity, and perseverance required to successfully pursue a treatment plan.

In fact, it has recently been confirmed that in the case of anxiety the best treatment involves teaching the patients new ways of responding to old stimuli. Drugs may be used to blunt the physical aspects, but there is no data to confirm the positive effects of their long-term use. Meanwhile, treatment of depressions requires attentive counseling and listening to the patient. The same applies to treatment of personality disorders, obsessive-compulsive disorders, hysteria, and paranoia. Unfortunately, cost of treatment and compliance with suggestions made by the therapist are major problems, as pointed out above.

In difficult cases observation and comparison with criteria compiled in the Diagnostic and Statistical Manual of Mental Disorders—the standard classification text of the American Psychiatric Association—are the only recognized treatment alternatives.

There is also a wide variety of medical conditions, other than the above-mentioned psychological disorders, requiring extensive self-help and self-treatment by the patient. These conditions include addictions, compulsive behaviors, and substance abuse. Most common examples are smoking, gambling, and alcoholism. At the present time treatment for these medical conditions involves counseling, distraction techniques, and chemical replacement therapy. Ultimately, however, all of these methods depend on the cooperation of the patient and a large dose of self-motivation. This is especially important when the patient is in his or her own surroundings where the objects of their addiction or compulsion are easily accessible.

Unfortunately, compliance with medical advice is notoriously poor, and gentle persistence may be necessary. Some physicians recommend that the entire family or other group of significant personal contracts in the patient's life should be involved with the patient's consent. This, of course, presents major problems and is a costly treatment method.

Some attempts have been made at using computers to diagnose and educate patients about their medical condition. Typically, these attempts have produced questionnaires which can be filled out on a computer, or educational programs telling the patient more about his or her medical condition. Unfortunately, these projects stop short of being sufficiently adapted to patient needs to help with treatment or therapy. In fact, health care professionals maintain that computers can never replace the sense of caring, of relatedness, which is the vehicle in which most therapy takes place.

OBJECTS AND ADVANTAGES OF THE INVENTION

Objects of the invention are to enable treatment in the patient's own, private environment, provide a treatment method to which the patient can resort as the need arises, and ensure higher treatment compliance for all patients, and in particular children.

These and other objects and advantages will become more apparent after consideration of the ensuing description and the accompanying drawings.

BRIEF DESCRIPTION OF THE DRAWINGS

FIG. 3 is a sample program assignment screen as displayed on the remote interface;

FIG. 4 is a sample report screen as displayed on the remote interface;

FIG. 5 is a sample interactive educational program as displayed by the multimedia processor;

DETAILED DESCRIPTION OF THE PREFERRED EMBODIMENTS

Figure 1:
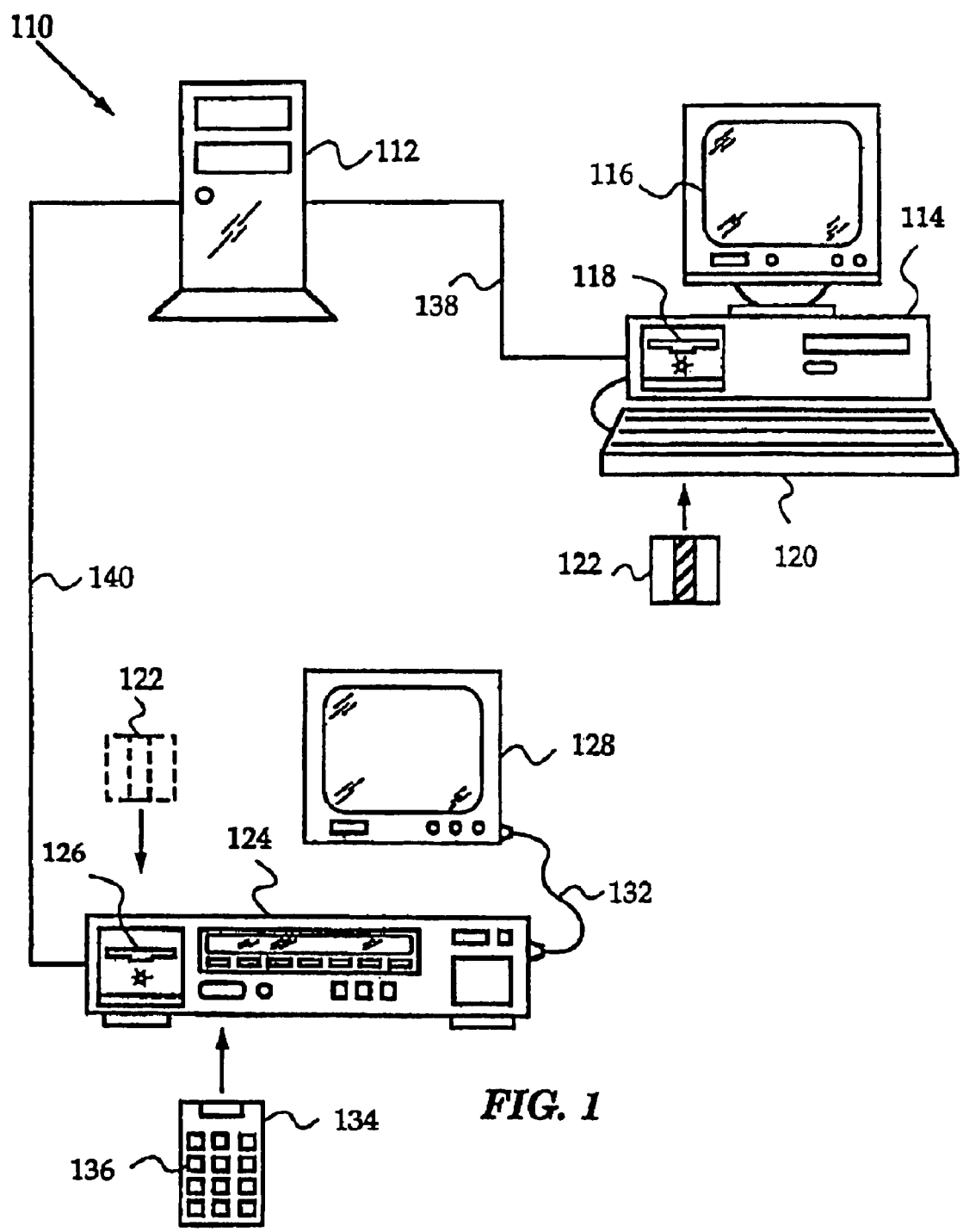
FIG. 1 is a schematic diagram of a remote education system according to a preferred embodiment of the present invention.

The preferred embodiment of the system is shown in FIG. 1. The system 110 comprises a file server 112, which is connected by communication links 138, 130, and 140 to a remote interface 114, a database 148 containing educational programs, and a multimedia processor 124. File server 112 is preferably a world wide web server, remote interface 114 is preferably a web page, and communication links 138 and 130 are preferably the Internet. Remote interface 114 has a display 116 and a keyboard 120, which an administrator can use to assign an educational program to an individual.

Remote interface 114 also contains or is connected to a memory card writer 118. Memory card writer 118 is used to record the individual's identification code and the location of file server 112 on a memory card 122. Preferably, the location of file server 112 is in the form of a uniform resource locator, or URL.

Communication link 140 from file server 112 to multimedia processor 124 is preferably the Internet. However, file server 112 and multimedia processor 124 can also contact each other via wireless communication networks, cellular networks, telephone networks, or any other suitable network. Multimedia processor 124 is also connected by communication link 132 to a display 128, which is used to show educational programs to the individual. Communication link 132 can be any suitable connection means. Display 128 is a standard audiovisual display, such as a television.

Multimedia processor 124 contains or is connected to a memory card reader 126. When memory card 122 is placed in memory card reader 126, the assignment information is sent to file server 112, which retrieves the assigned educational program from database 148. The educational program content is then sent through communication link 140 to multimedia processor 124 and shown on display 128. In addition, microprocessor 124 can also comprise expansion ports to support additional user interfaces and devices, such, as keyboards and trackballs, as well as add-on circuits for enhanced sound, video, or processing performance (not shown).

As shown in FIG. 3, input device 134 comprising numerous momentary contact push buttons 136 is used by the individual to control and respond to the educational program. Push buttons 136 represent control functions, such as "on" and "off", as well as numbers, letters, or various commands, such as "yes" and "no". Alternatively, push buttons 136 may be replaced by switches, keys, a touch sensitive display screen, or any other data input device. Input device 134 is a standard wireless communication means which sends command signals to multimedia processor 124 to be processed and executed. However, any communication means which allows input device 134 to connect with multimedia processor 124.

For clarity of illustration, only one database and only one multimedia processor are shown in FIG. 1. It is to be understood that system 110 may include any number of databases for storing any number of educational programs, and any number of multimedia processors for use by any number of individuals.

Figure 2:
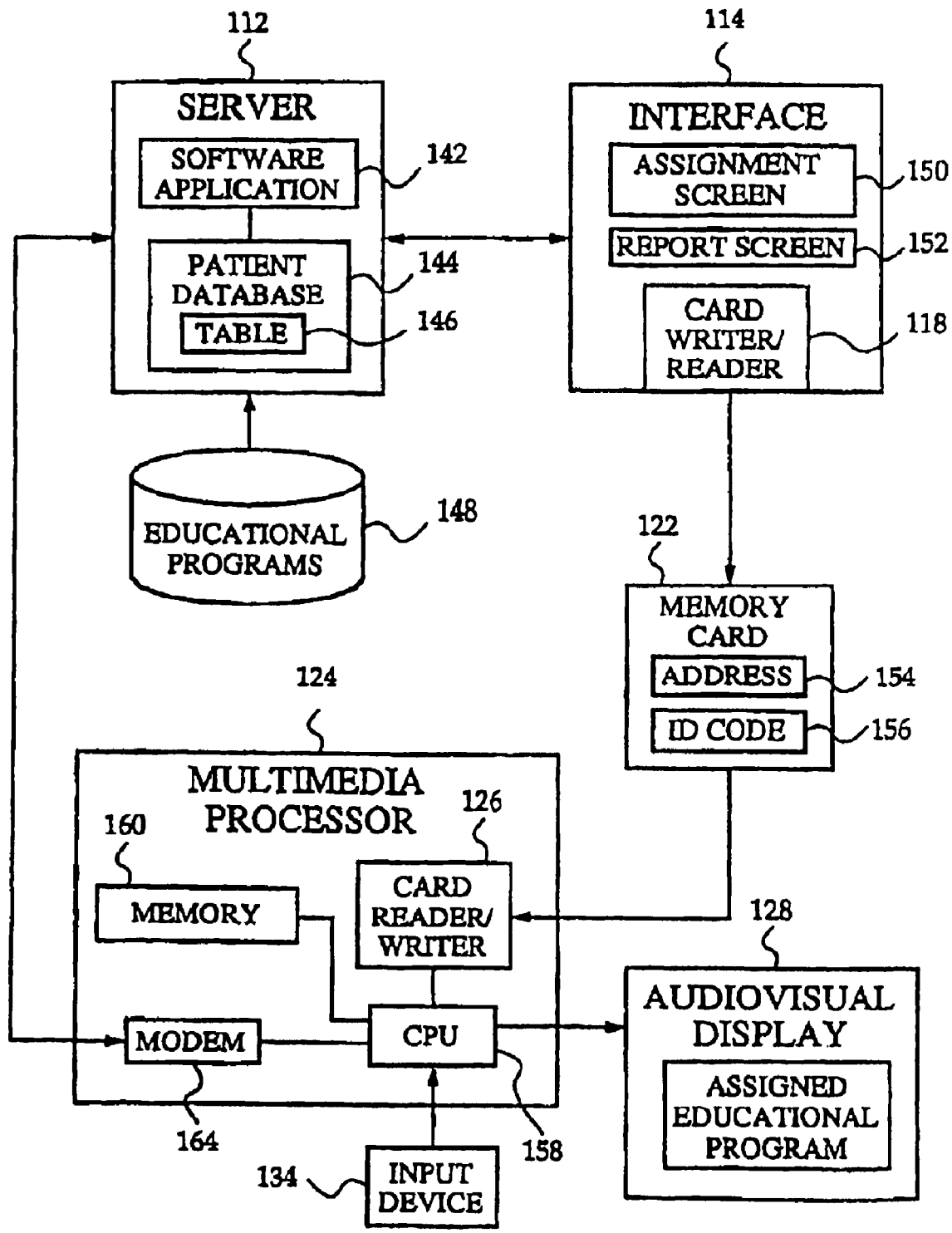
FIG. 2 is a block diagram showing the components of the remote education system and how they are connected, according to FIG. 1.

FIG. 2 shows a detailed block diagram of the preferred embodiment of the invention illustrated in FIG. 1. Server 112 includes a general software application 142 which is used create a database 144 and a patient table 146. Software application 142 is also capable of programming file server 112 to carry out standard commands such as receiving, saving, and transmitting information. Database 144 contains the educational programs 148. Alternatively, database 144 can contain pointers to educational programs 148 which are located in remote databases. The advantage of the pointers is that they allow the healthcare provider to assign any number of educational programs 148, as long as educational programs 148 can be transmitted to multimedia processor 124 and shown on display 28. Thus suitable forms of educational programs 148 include photos, videos, animation, static web pages, interactive web pages, etc. Patient table 146, which is stored in the memory of file server 112, lists the patients, their identification codes, and educational programs 148 which have been assigned to them.

Patient table 146 is generated by information entered into the assignment screen 150 of remote interface 114. Assignment screen 150, which is illustrated in FIG. 3, lists available educational programs 148, each with a corresponding check box 166, and patients, also each with a corresponding check box 168. The administrator brings up assignment screen 150 on display 116 of remote interface 114. She selects a check box 168 for a patient and then selects a check box 166 corresponding to educational program 148 to be assigned to the patient. More than one educational program 148 can be assigned to each patient. In addition, more than one patient can be assigned the same educational program 148. The administrator then selects the ASSIGN PROGRAM button 170, which stores the assignment in patient table 146. Assignment screen 150 also includes a DELETE PROGRAM button 172, which allows the administrator to erase the assignment.

New listings of patients and educational programs 148 can easily be created by the administrator by clicking on the ADD NEW PATIENT button 174 or the ADD NEW PROGRAM button 176. When these buttons are selected, a new field is added to the patient or program categories. The administrator then types in the name of the new patient or the name of the new educational program 148, and saves the addition by clicking on the SAVE NEW LISTING button 178. The new listings are then saved in patient table 146.

In the preferred embodiment, remote interface 114 is a web page. Thus, using keyboard 120, as shown in FIG. 1, the administrator can create customized educational programs 148 in the form of static or interactive web pages for patients. The administrator creates the web page using a scripting language such as HTML or Java, and then stores it on database 144. These web pages can be accessed by multimedia processor 124 in the same manner as the above mentioned educational programs 148.

Referring to FIG. 2 again, remote interface 114 also comprises a report screen 152 which is shown on display 116. Report screen 152, as illustrated in FIG. 4, tells the administrator when the patient has completed watching assigned educational program 148 and/or a program score. Specific techniques for writing report generator program to display data in this manner are well known in the art.

The program score is generally determined by evaluating the patient's responses to an interactive educational program, such as an interactive web page. FIG. 5 shows a sample educational program 148 which includes questions for the patient to answer using input device 134.

The remote education system also includes a memory card writer 118 connected to remote interface 114. Memory card writer is an apparatus which can encode information onto a magnetic strip or circuit. The process of storing information on a magnetic strip or circuit is well known. Memory card 122 produced contains the patient's identification code 156 and the file server address 154.

As shown in FIG. 2, multimedia processor 124 also comprises a memory means 160, a central computing unit (CPU) 158, a modem 164, and audiovisual display 128. Memory card reader 126, memory means 160, modem 164, and audiovisual display 128 are all connected to CPU 158. Multimedia processor 124 connects to file server 112 using modem 164 and communication link 140, which is preferably a telephone cable. Multimedia processor 124 can be programmed to automatically dial out using modem 164 whenever memory card 122 is placed in memory card reader 126.

Memory card reader 126 comprises means of detecting and interpreting the information stored on memory card 122. In the preferred embodiment, memory card reader 126 is a magnetic strip reader. When the patient places memory card 122 in memory card reader 122, the information is sent to CPU 150 and then memory means 160. The information is then sent to file server 112 by way of modem 164.

Memory means 160 of multimedia processor 124 is also for storing program instructions on how to connect to file server 112 and how to transmit patient's identification code 156. In addition, memory means 160 receives and stores assigned educational programs 148 from file server 112. When the content of educational programs 148 are sent to multimedia processor 124 from file server 112, memory means translate the content into audiovisual signals to be displayed on display 128.

Figure 6A:
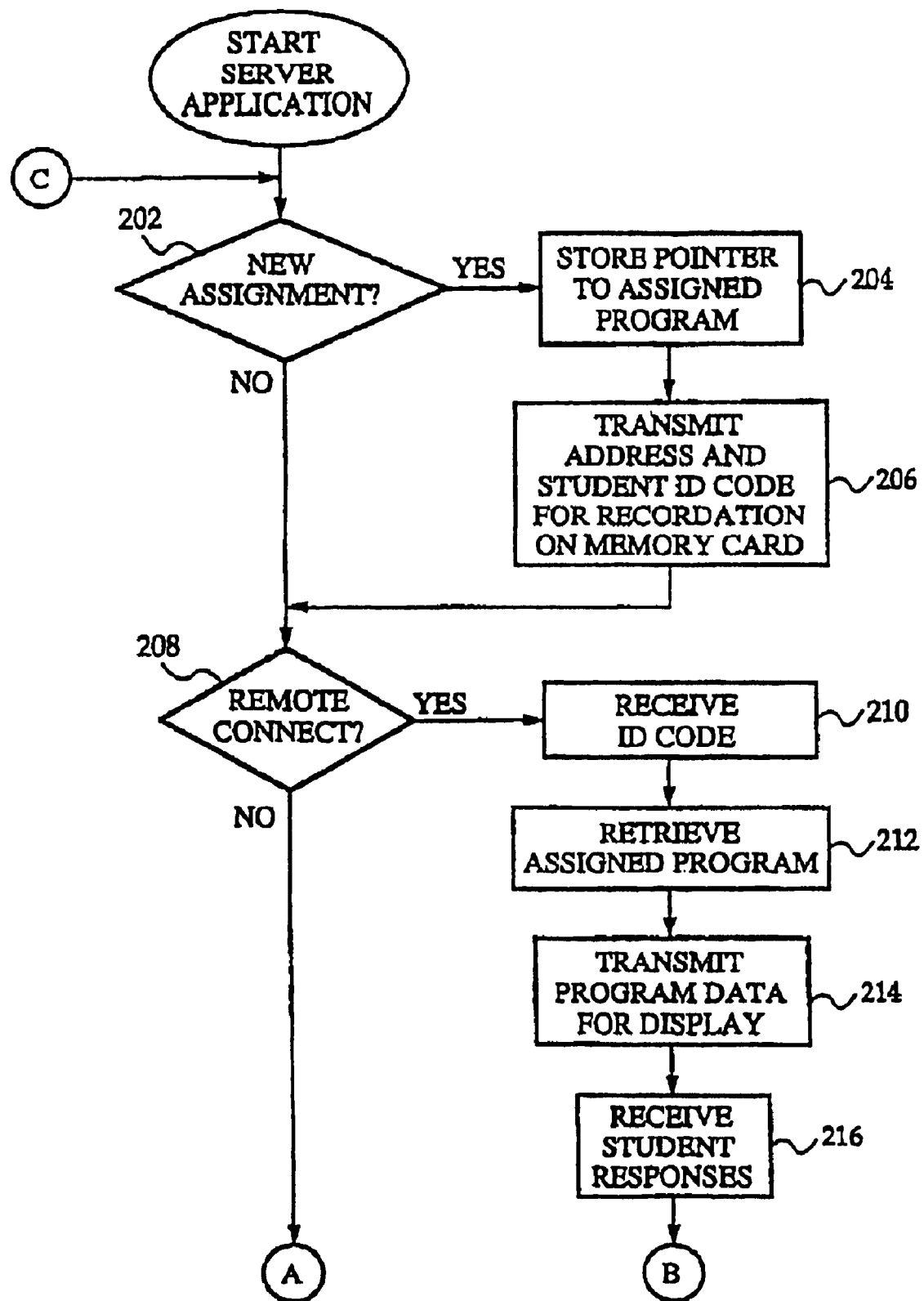
FIG. 6A is a flow chart illustrating the steps executed by the file server of the present invention as shown in FIG. 1.
Figure 6B:
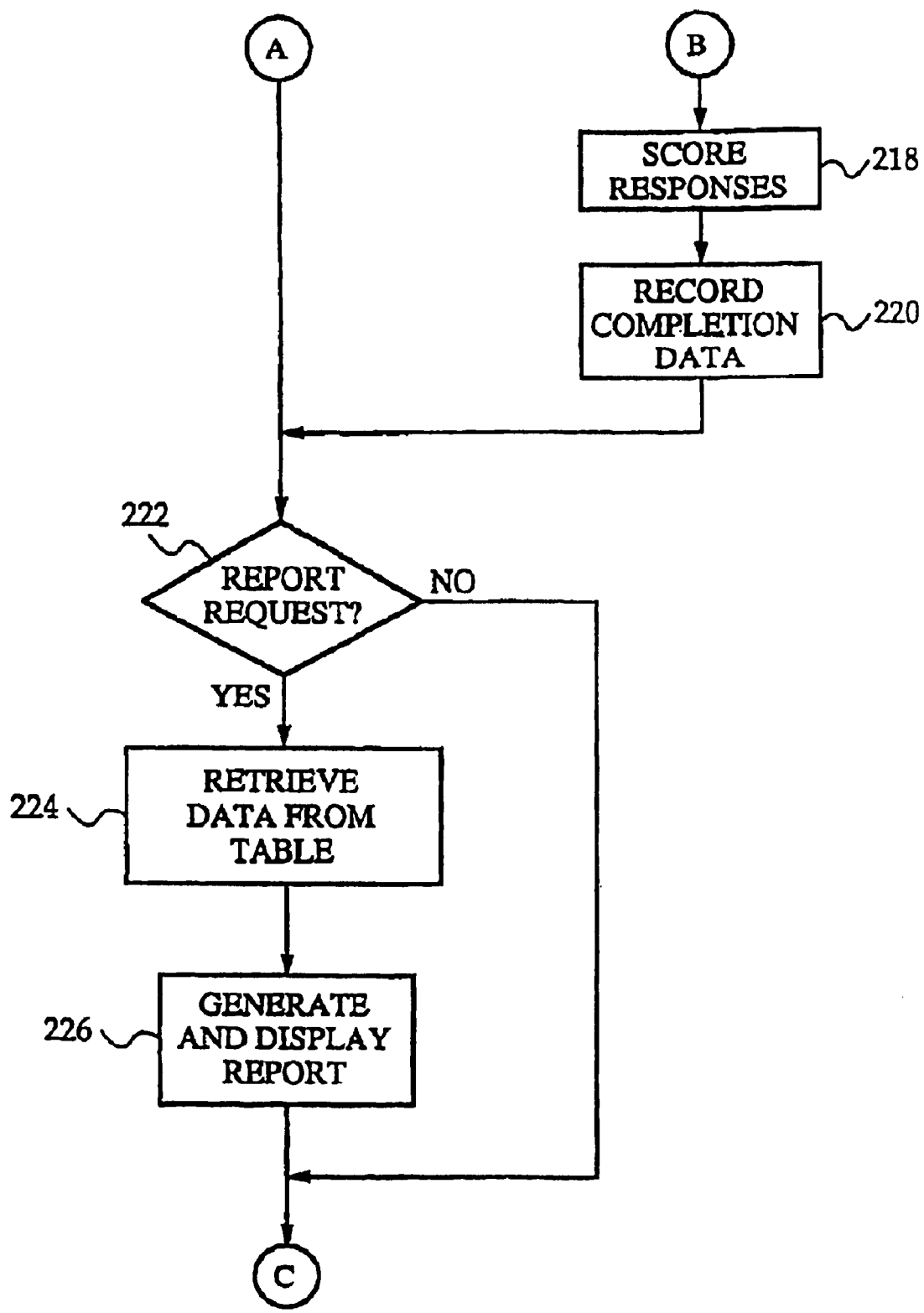
FIG. 6B is a continuation of the flow chart of FIG. 6A.

FIGS. 6A and 6B show a flowchart illustrating the steps carried out by server 112 in the preferred embodiment of the invention. In step 202, server 112 first asks if the administrator would like to create a new assignment. Creating a new assignment can mean adding a new patient to the patient list or assigning a new educational program 148 to a patient. If the administrator decides to create a new assignment, the information is stored in patent table 146, as shown in step 204. In step 206, the new assignment information consisting of the patient's identification code 156 and file server address 154 is also recorded on memory card 122 by memory card writer 118, and then given to the patient. If the administrator does not need to create a new assignment, she goes directly from step 202 to step 208.

After the patient returns home, he places memory card 122 in memory card reader 126 connected to multimedia processor 124. File server address 154 on memory card 122 allows multimedia processor 124 to locate and connect to file server 112 in step 208. Patient's identification code 156 is then sent over in step 210. In step 212, file server 112 then goes to patient table 146 and looks up educational program 148 assigned to patient. A pointer in database 144 then retrieves educational program 148. If educational program 148 is located in a remote database, it is sent through file server 112 to multimedia processor 124, as shown in step 214. Memory means 160 of multimedia processor 124 then interpret and translate the content of educational program 148 into audiovisual signals to be shown on display 128.

After the patient has watched educational program 148, completion data comprising the time and date or patient responses is sent from multimedia processor 124 to file server 112 in step 216. Step 218 scores the patient responses to determine a program score. Step 220 then records the completion data in patient table 146 of file server 112.

If the administrator wishes to view completion data of a particular patient, she can request a patient report, as shown in step 222. Step 222 can occur after the patient has watched and responded to educational program 148 in step 220, or at any time after step 208. File server 122 retrieves the patient's completion data from patient table 146, step 224, and then shows it in the form of report screen 152 on display 116 in step 226. Report screen 152 is illustrated in FIG. 4.

Figure 7:
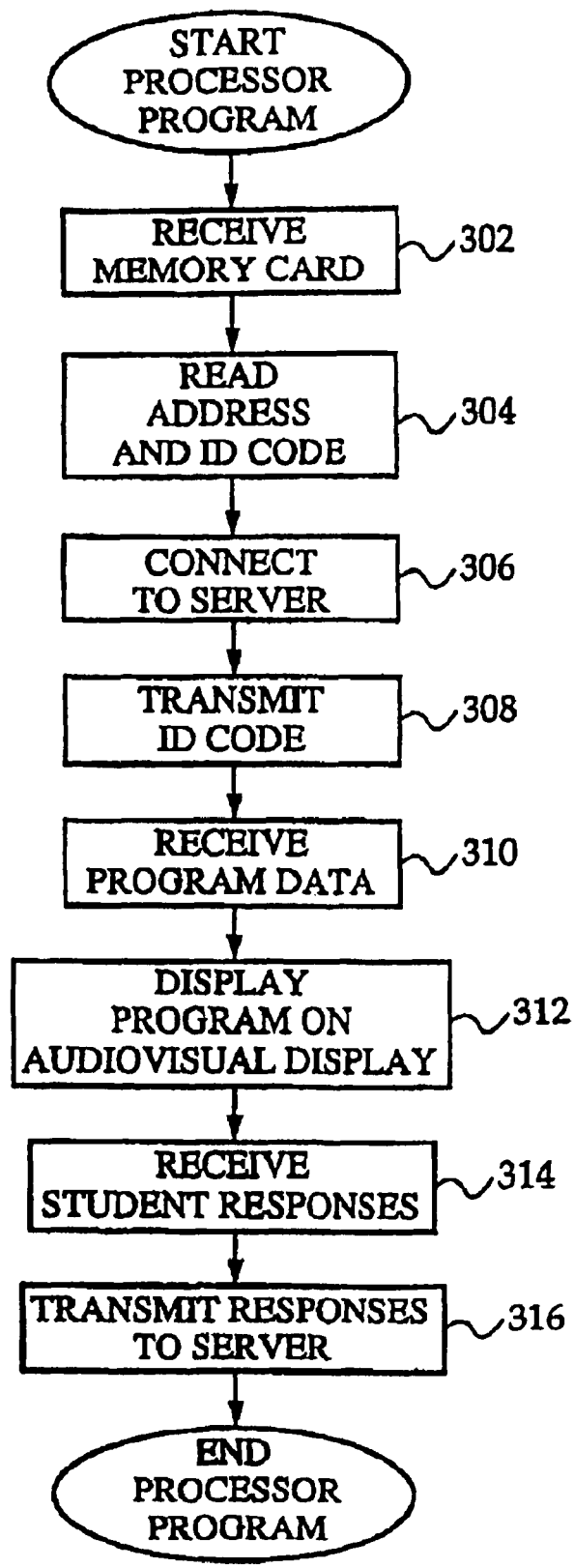
FIG. 7 is a flow chart illustrating the steps executed by the multimedia processor of the present invention as shown in FIG. 1.

FIG. 7 is a flowchart outlining the steps involved in the processor program of multimedia processor 124 in the preferred embodiment of the invention. Processor program can be carried out by known software programs. The processor program begins when memory card 122 is placed in memory card reader 126, as shown in step 302. Memory card reader 126 reads patient's identification code 304 and file server address 156 from memory card 122 in step 304, and then sends the information to CPU 158. File server address 154 allows CPU 158 to connect to server 112 via modem 164 in step 306. Patient's identification code 156 is then transmitted to file server 112 in step 308. In step 310, CPU 158 receives the content of assigned educational program 148 via modem 164. The content is converted into audiovisual signals shown on display 128 in step 312. Patient response to educational program 148 is sent to CPU 158 by input device 134. CPU 158 then sends the patient response, along with other completion data, to file server 112. The processor program of multimedia processor 124 then ends.

Memory card reader 126 of multimedia processor 124 can also have a writing function similar to that of memory card writer 118 of remote interface 114. This feature allows the patient responses to educational program to be stored on memory card 122. The patient can then bring in memory card 122 to his healthcare provider or the administrator. Memory card writer 118 of remote interface 114 must also have reading capabilities. Memory card 122 is inserted in memory card writer/reader 118 and the patient responses are downloaded into remote interface 114. This feature can be used if the patient does not wish to transmit his responses over communication link 140.

The present invention allows a healthcare provider or administrator to assign a remote educational program to a patient. The patient has the luxury of watching and responding to the program in his own home at his convenience. The patient's response to the educational program is then transmitted to the file server and displayed for the administrator to view. Thus the administrator can monitor whether or not the patient has watched the educational program, and can also evaluate his responses to the program.

Appendix A shows one implementation of the present invention as it applies to working with a diabetes patient through MEDTV.™ over the Internet. MEDTV.™ is a trademark of Raya Systems, Inc. (Mountain View, Calif.).

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible, as this invention can be used in any field where it is desirable to remotely educate an individual. For example, teachers can use it to assign lessons to their students, and employers can use it to provide additional job training for their employees.

Another embodiment of the present invention allows companies to promote their products. Preprogrammed memory cards can be placed with a company's products. When the consumer buys a product, he also receives the preprogrammed memory card, which contains the product identification code and the address of the company's consumer-product file server. When the consumer places the memory card in the memory card reader of his multimedia processor, the multimedia processor automatically connects to the company's file server. The file server contains a consumer-product table which stores a list of all the company's products with corresponding pointers to relevant educational programs or advertisements. For example, a sunblock product would have a pointer to a short video on basic sun safety, as well as an advertisement for all sunblock products made by that company.

When the file server receives the product identification code from the multimedia processor, it retrieves the relevant educational program or advertisement and sends it back to the consumer's multimedia processor. The consumer can then watch the program or advertisement on the display.

Considering all the possibilities of the remote education system, the scope of the invention should be determined not by the examples given, but by the appended claims and their legal equivalents.

Figure 8:
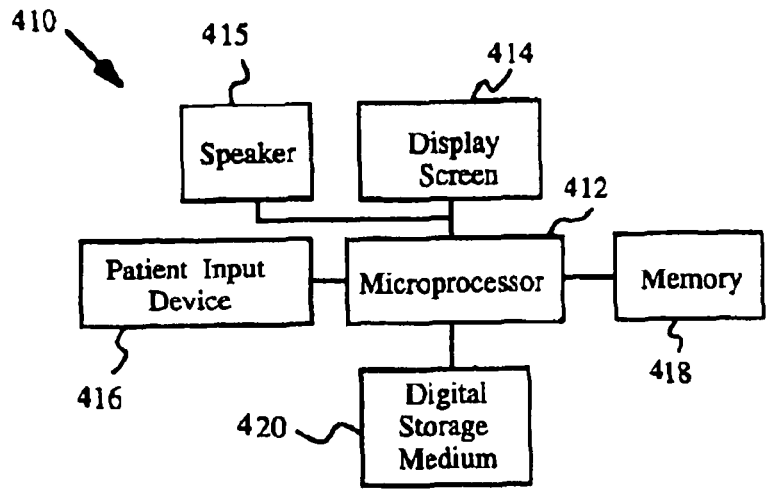
FIG. 8 is a block diagram of an autonomous computer system employed in the method according to the invention.

FIG. 8 shows a block diagram representing a typical embodiment of a computer or microprocessor-based unit 410 capable of supporting video games for patient treatment. At the heart of unit 410 is a microprocessor 412. In addition to operations necessary to run unit 410, microprocessor 412 can process video data. Of course, in complicated systems the tasks of microprocessor 412 can be performed by a number of microprocessors. In the most preferred embodiment microprocessor 412 is a SUPER NINTENDO™ microprocessor.

A display unit or screen 414 is connected to microprocessor 412. The resolution and size of display screen 414 are sufficient to project visual images generated by video games. In a preferred embodiment screen 414 is a high-resolution video monitor or television screen. A speaker 415 for producing sounds associated with video games is hooked up to microprocessor 412 as well.

A patient input device 416 is also connected to microprocessor 412. Input device 416 can be a keyboard, joystick, mouse, button, trigger, light-pen, or the like, or combinations of these devices. A suitable choice of input device 416 is made based on the video game displayed on display screen 414 and the medical conditions of the human patient. The selected input device 416 will thus permit the patient to actively participate in the video game.

Additionally, microprocessor-based unit 410 has a memory 418, which is in communication with microprocessor 412. Memory 418 contains data required by microprocessor 412 to operate unit 410. While in the exemplary embodiment illustrated in FIG. 8 memory 418 consists of a single unit, configurations with many memory units of different types are possible.

Unit 410 is also connected to a digital storage medium 420 and appropriate data reading devices (not shown). Digital storage medium 420 can be a hard-disk, a floppy disk, a compact disk (CD), a cartridge, a network storage unit, or any other convenient medium capable of storing electronic instructions for running a video game on unit 410. In the preferred embodiment storage medium 420 is a high-storage-capacity CD disk. The ability to hold a large amount of data is a prerequisite for storing large video game programs.

Figure 9:
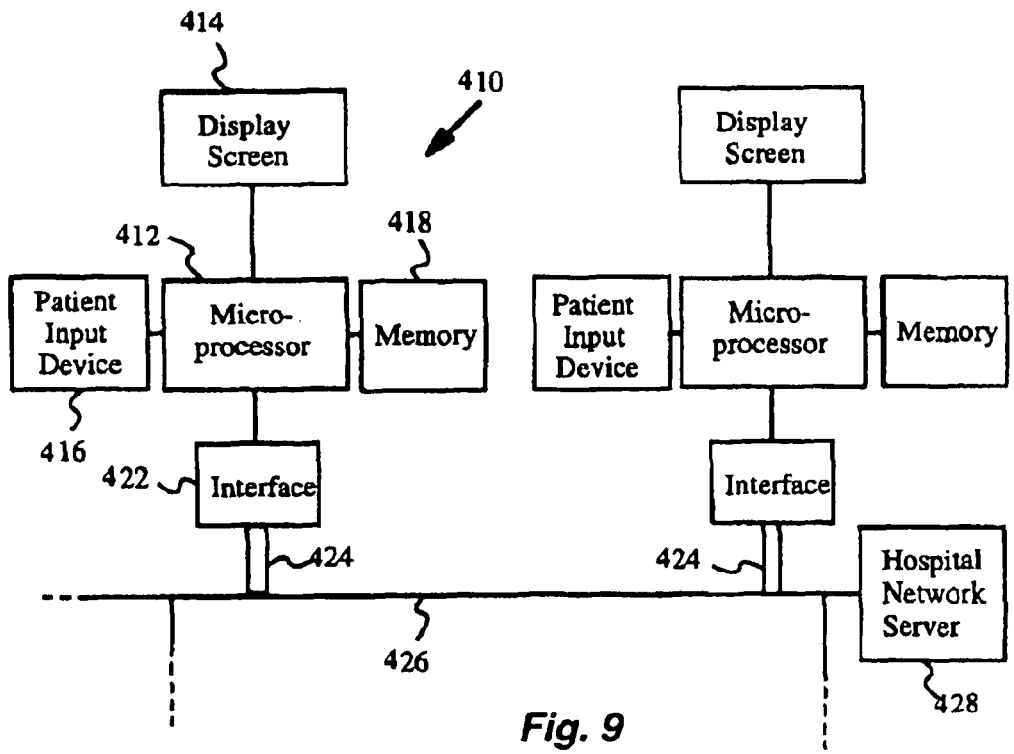
FIG. 9 is a block diagram of a computer network used in the method according to the invention.

FIG. 9 is a block diagram of a computer network for practicing the video game treatment method. Individual microprocessor-based units 410 on the computer network are substantially the same as in FIG. 8, therefore the same reference numbers are used for corresponding parts. Instead of digital storage medium 420, units 410 in FIG. 9 have a network interface 422 equipped with a network link 424. Link 424 connects microprocessor 412 to network 426 via interface 422. In a preferred embodiment network 426 is a separate hospital network adapted to patient use.

On the hospital side network 426 is connected to a hospital network server 428. Server 428 is capable of exchanging data, in particular video game data, with each unit 410 connected to network 426. Server 428 is also connected to computers used by monitoring personnel and physicians at the hospital (not shown).

Figure 10:
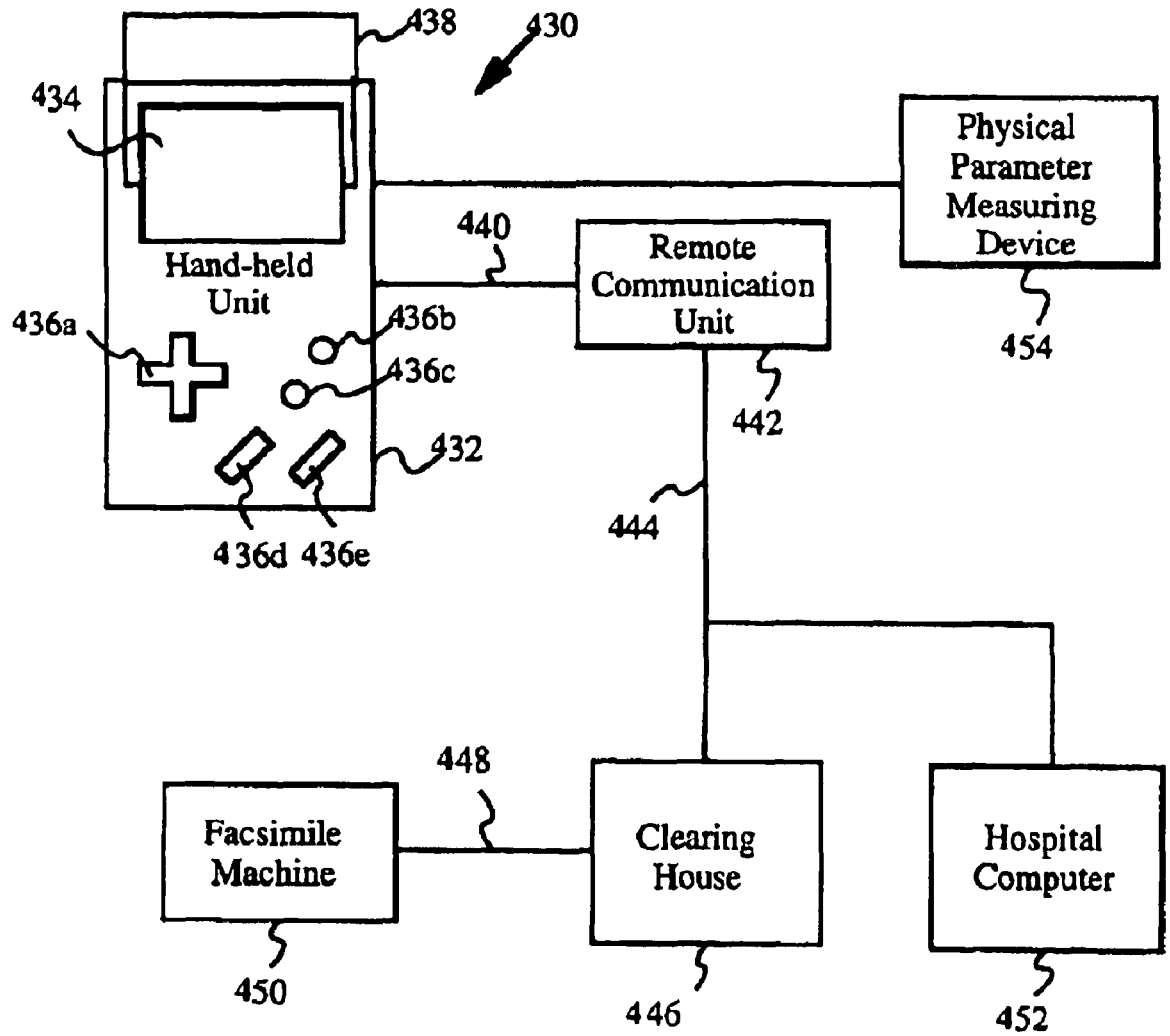
FIG. 10 is a block diagram of a system employing a hand-held: microprocessor unit for implementing the method of the invention.

The block diagram of FIG. 10 shows a particularly convenient embodiment for implementing the diagnosis and treatment method. A hand-held microprocessor unit 430 is equipped with a video display 434 and a number of input switches or keys 436a, 436b, 436c, 436d, and 436e, which are mounted on a housing 432. A set of components including a microprocessor, memory circuits, and circuitry that interfaces keys 436a, 436b, 436c, 436d, and 436e with the microprocessor is installed inside housing 430 but not shown in FIG. 10. Stored in the memory of programmable hand-held microprocessor unit 430 is a set of electronically encoded program instructions. These instructions establish a data protocol that allows hand-held microprocessor unit 430 to perform digital data signal processing and generate desired data or graphics for display on display unit 434 when a program cartridge 438 is inserted into a slot or other receptacle in housing 432. That is, cartridge 438 of FIG. 10 includes read-only memory data encoding the instructions for playing a particular video game.

In the most preferred embodiment hand-held microprocessor unit 430 is the compact game system manufactured by Nintendo of America, Inc. under the trademark "GAME BOY". This device is particularly simple. Furthermore, unit 430 is hooked up to a remote communication unit 442 via a connection cable 440. Preferably, for reasons of convenience, unit 442 can be a modem capable of communicating over telephone lines, or a radio-frequency transceiver capable of wireless sending and receiving of information. Of course, any other common telecommunications devices can also be used. It is assumed in the preferred embodiment shown in FIG. 10 that unit 442 is a high-speed modem.

A communication line 444, in this event a telephone line, connects unit 442 to a data clearing house 446 and hospital computer 452. This set-up establishes an efficient data pathway from hand-held microprocessor unit 430 to clearing house 446 and hospital computer 452. Clearing house 446 is capable of classifying data and sending appropriate messages concerning the patient's medical condition to a health care professional or physician. In the preferred embodiment clearing house 446 is connected by transmission line to a facsimile machine 450 standing in the office of a physician or health care professional.

A physical parameter measuring device 454, e.g., a glucose blood meter or a respiratory flow meter is also connected to hand-held unit 430. Device 454 is designed for patient self-monitoring while playing a video game. For this purpose device 454 is capable of downloading measurement data into hand-held unit 430. Appropriate choice of device 454 is made by the physician depending on the other hardware and intended video game for patient treatment.

Operation—FIGS. 8 to 17

Figure 11:
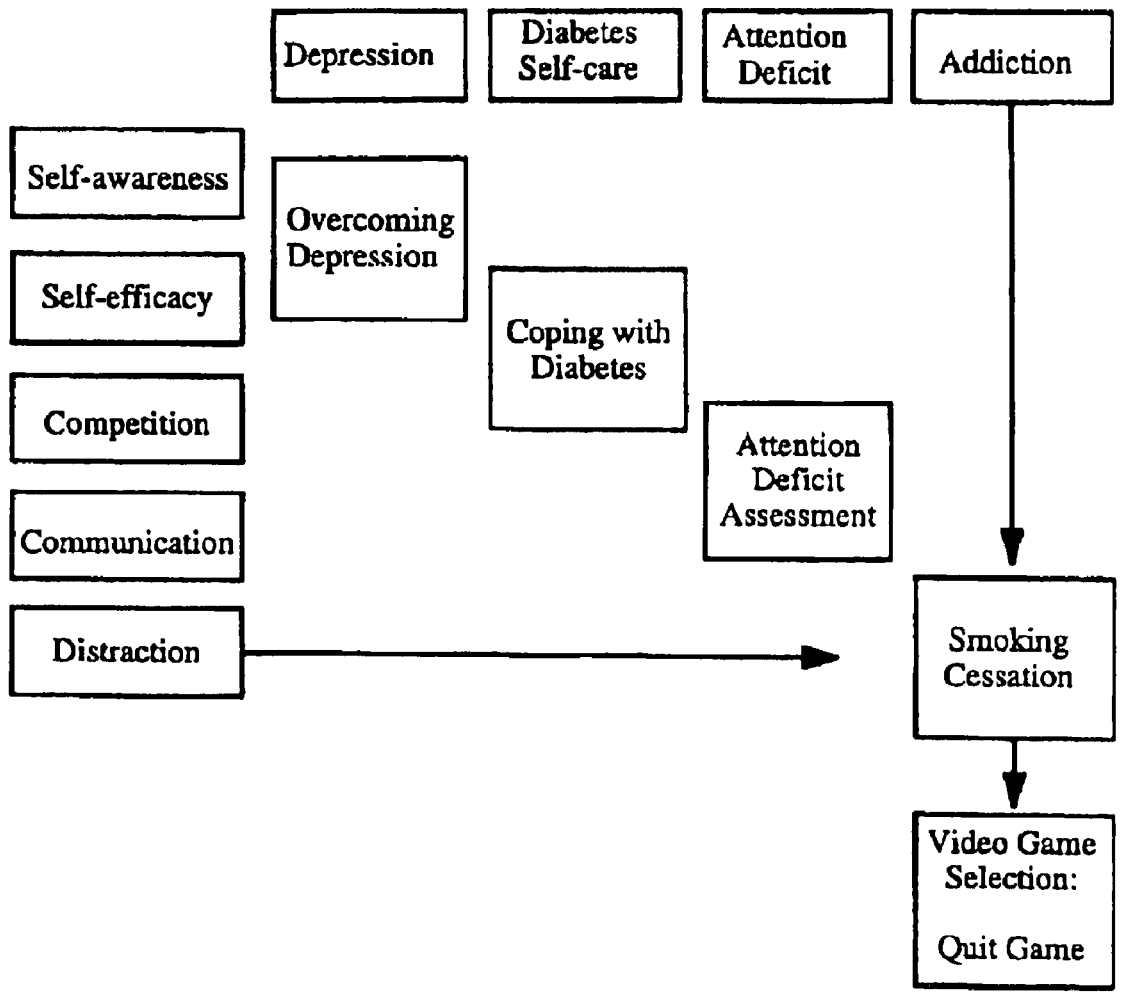
FIG. 11 is a flow chart illustrating how to select an appropriate video game treatment for some common medical conditions.

Before using microprocessor-based unit 410 shown in FIG. 8, a patient will first visit a physician or health care professional to evaluate his or her medical condition. The physician will diagnose the condition and choose the proper treatment based on patient needs. The flow chart in FIG. 11 shows the psychological strategies which the physician can select for treating depression, attention deficit, addiction, and diabetes. The psychological strategies listed include self-awareness training, self-efficacy training, competition, communication, and distraction. Of course, other well-known strategies such as positive reinforcement, negative reinforcement, role-playing, etc. can be employed as well. In addition to these, the psychological treatment strategy can include counseling methods and self-care instructions. Moreover, the treatment strategies can be combined as shown For example, as shown in FIG. 11, overcoming depression is best ensured by a therapy which joins self-awareness training with learning self-efficacy to regain control over one's life. In the particular case highlighted with two arrows the medical condition to be treated is an addiction, e.g., smoking or alcoholism, and the appropriate psychological strategy for treating this condition is distraction.

Once the psychological treatment strategy has been selected, the physician will choose an appropriate interactive video game program comprising this strategy. Examples of video games based on the most common psychological strategies will be given in the specific examples to follow. Meanwhile, the program itself consists of electronically encoded instructions in data storage medium 420 (FIG. 8). The video game program is loaded from this medium 420 into microprocessor 412 and memory 418 of unit 410. In the preferred embodiment this is accomplished most conveniently by a CD disk drive (not shown) since digital storage medium 420 is a CD disk. The patient receives unit 410 prepared in this way and is instructed by the physician how and when to play the video game. Of course, the physician may also load several video games at once and instruct the patient when to play each one. Depending on the type of video game and the patient's capabilities, the physician will also determine what patient input device 416 should be employed in playing the game.

The patient takes home unit 410 prepared in this manner, and follows the prescribed treatment by playing the video game. Once in operation, unit 410 displays the graphical video game on display screen 414 and receives input through patient input device 416. The beneficial effect of playing the game is thus available to the patient at any time in his own environment.

The process described above can also be accomplished with the computer network shown in FIG. 9. Here, appropriate treatment programs can be loaded directly into unit 410 used by the patient while he is at home. To do this the physician selects the appropriate video game, determines its destination address, i.e., unit 410, and places the game on hospital network server 428. The designated unit 410 then retrieves the video game via network 426 and loads it into microprocessor 412 and memory 418. This is done with the aid of network link 424 and interface 422.

A particularly convenient method for delivering a video game to the patient is shown in FIG. 10. Hand-held microprocessor unit 430 receives video games directly from hospital computer 452. The video game is transmitted through communication line 444 and received by remote communication unit 442. Unit 442 downloads the game directly into hand-held unit 430 via connection cable 440.

Hand-held unit 430 in FIG. 10 also communicates with clearing house 446 using communication line 444. Thus, the patient's progress in playing the video game can be directly monitored, e.g., by checking the video game scores. This information is screened, classified, and sorted by clearing house 446. Then an abstract or report is transmitted through transmission line 448 to facsimile machine 450 which can be conveniently located in the physician's office.

Unit 430 shown in FIG. 10 can also be used by the patient to check his medical condition. To do this the patient follows instructions embedded in the video game which tell him to connect to unit 430 his measuring device 454, e.g., blood glucose meter in the case of a patient with diabetes. Of course, unit 430 and device 454 may also be hooked up permanently by the physician. Then the video game instructions tell the patient that to continue playing he needs to perform a regular self-measurement using device 454.

For a patient with diabetes this involves checking his blood glucose level by drawing a small blood sample into device 454. The individual steps for doing this are not a part of the invention. The measurement data is then downloaded into hand-held unit 430 to be used as input for the interactive video game session. Exemplary video game using this technique to collect data is described in example 4 below. Meanwhile, the blood glucose data is also passed through cable 440 to remote communication unit 442. From there the data follows the same path as described above for the video game score, and can be examined by the physician in the hospital.

The specific examples below describe exemplary microprocessor-based, interactive video games used for treating various medical conditions in human patients.

Smoking

EXAMPLE 1

Figure 18A:
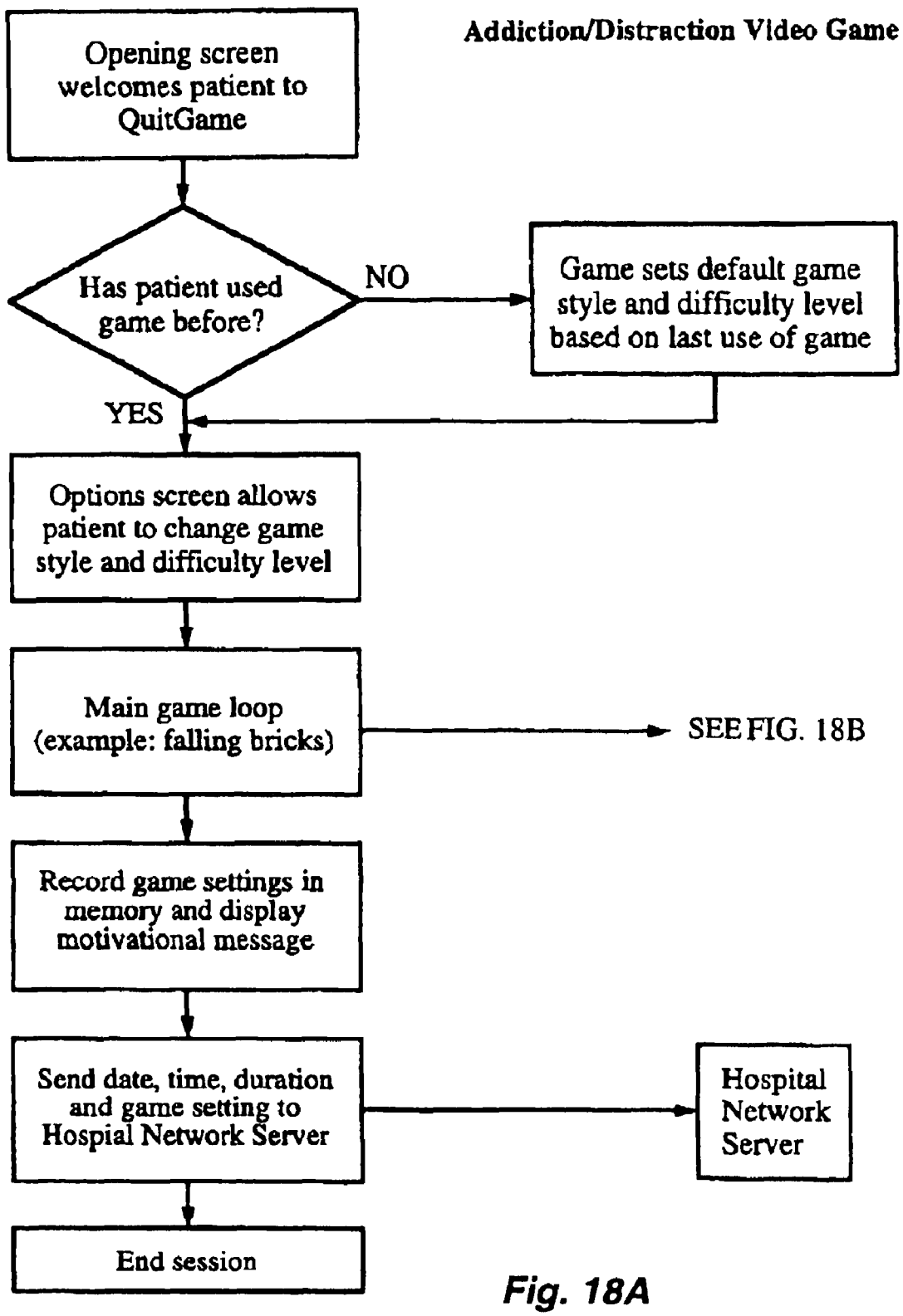
FIG. 18A is a general flowchart of an Addiction/Distraction Video Game.
Figure 18B:
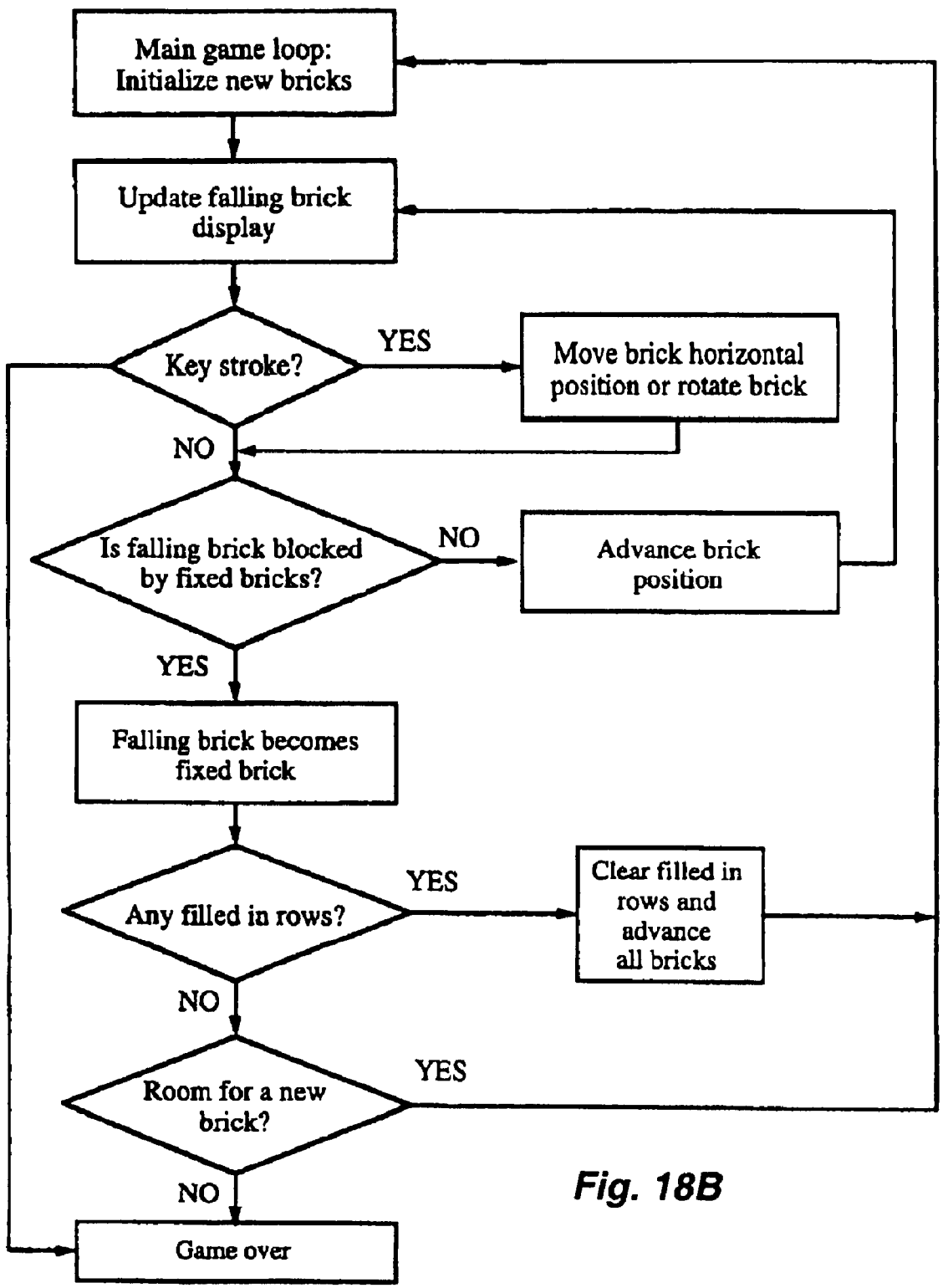
FIG. 18B is a detailed flowchart of the main game loop of the Addiction/Distraction Video Game of FIG. 18A.

The patient has a severe case of nicotine addiction. The physician determines, according to the flow chart in FIG. 11, that distraction is the best psychological strategy to induce the patient to quit smoking. Therefore, the physician prescribes playing the Quit Game, a video game containing a behavioral program based on distraction. This game contains graphical game characters engaging in various competitive activities upon proper input from the user. The smoker plays the game is played whenever he or she feels the urge to smoke. An exemplary game to provide such engaging distraction is shown in the flowchart illustrated in FIGS. 18A and 18B. In this particular embodiment the game distracts the player with falling bricks which have to be arranged in rows. During the game the main characters communicate to the patient instructions and simple strategies to quit smoking immediately and advise the user to take this approach, all within the context of the entertaining video game.

Alternatively, the game provides a timer and timeline for gradual reduction approaches to smoking cessation. Included among these programs are instructions for using nicotine patches. Built in notification will serve to remind smokers to shift to a lower dose patch. Once the smoker has quit, the video game will provide a coping/relapse prevention model by using distraction methods during periods of smoking urges.

A pilot study using the NINTENDO GAME BOY® as a tool to aid smoking cessation was highly successful. In the pilot project, seven smokers were give a Game Boy portable loaded with the Quit Game and instructed to use it any time they felt the urge to smoke. Six of the seven smokers successfully quit and were very enthusiastic about this approach.

An analogous video game strategy is followed in dealing with other substance abuse conditions, alcoholism, and obsessive compulsive disorders.

Growth Disorder

EXAMPLE 2

Figure 19:
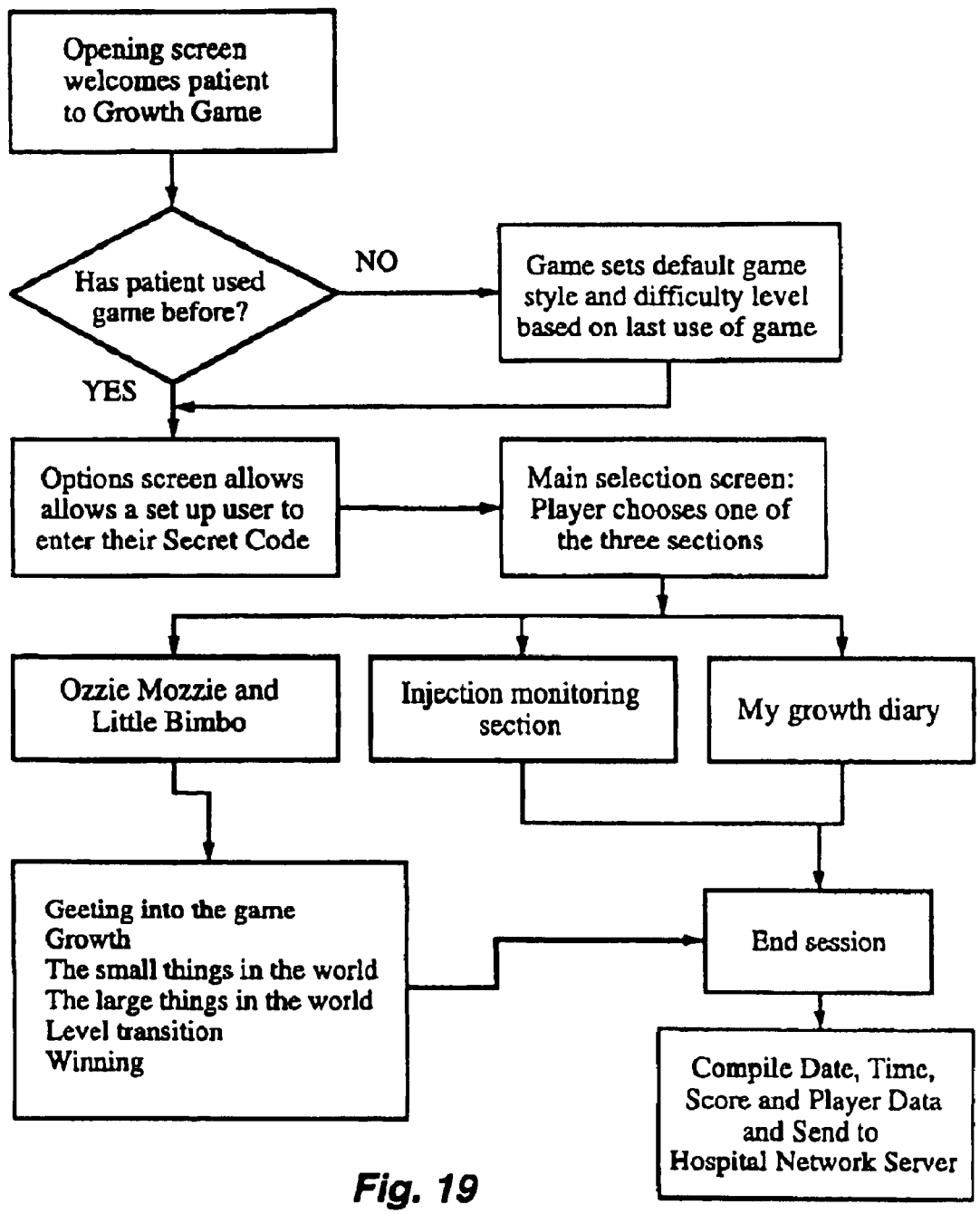
FIGS. 19-20 provide further illustrative flow charts.

The physician diagnoses the patient with a growth disorder, such as Turner's Syndrome or a similar condition, requiring growth hormone treatment and a psychological treatment strategy for helping the patient cope with his or her condition. By following a selection process similar to the one indicated in FIG. 18A-18B, the physician prescribes a video game combining self-awareness training, self-efficacy, role-playing, counseling and competition. The flowchart of the Growth Game is provided in FIG. 19.

In the video game the graphical game character, Packy, is a young elephant who, like the patient, is on growth hormone therapy. The video game consists of three pans, each associated with a particular aspect of the treatment. In the first part Packy encounters obstacles which he must surmount, in the second he has to learn about growth hormone injections, and in the third one he has to keep a personal growth diary.

Figure 12:
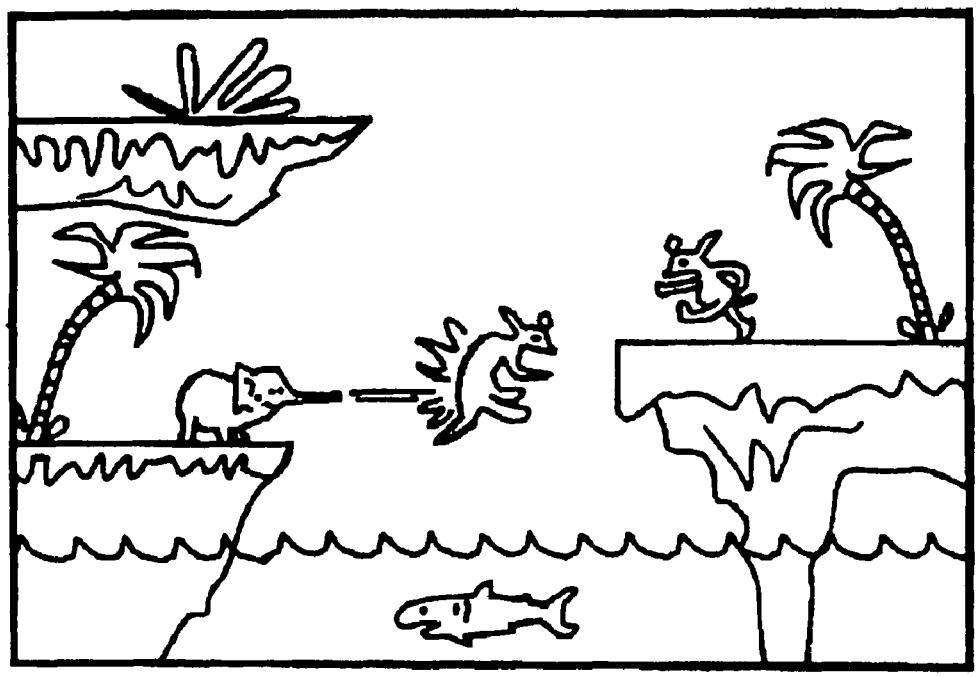
FIG. 12 is an exemplary screen of a video game for treating growth disorders according to the invention.

In the first part Packy learns about things that grow, from the smallest things in the world to the largest ones. In each level of this part Packy can pick up icons of OM (representing a growth hormone shot) for a boost of energy. When he gets this boost, he will grow to a larger size until the energy wears off or he gets hit by one of his opponents. Every time Packy meets someone who challenges him he must push them away by pressing a button to lower his head and walking into them, or squirt them by pressing another button. The small antagonists push and squirt away easily, but the large ones require some strategy such as combining pushing and squirting. This stage is depicted in FIG. 12. In each level Packy will occasionally find obstacles that require a growth shot to get past. He will also occasionally encounter a guardian to the pathway that asks him questions from the information learned in the other two parts, i.e., the growth hormone injection instructions and the personal growth diary.

Figure 13:
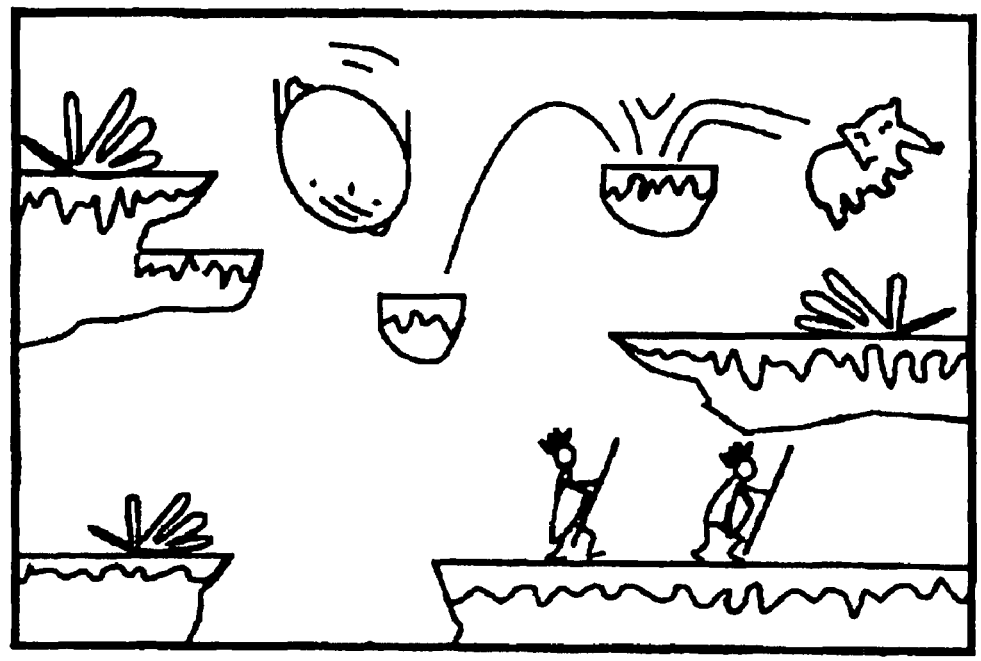
FIG. 13 is another screen of the video game of FIG. 12.

In another level of part one Packy has a dream in which he explores the world as a tiny creature. This scenario is illustrated in FIG. 13. He finds that he is very small himself, while all the surrounding items are very large. As he works his way to the end of this level he will encounter all types of animals and insects that are very small. This level will give Packy a feeling for what it is like to be really small. In the transition to the next level, Packy will wake up and see that he is still the same size, and grateful that he is not so small.

In the final level, Packy finds himself very large. He will be with the giant animals of the world. As he works his way through this level he will encounter all types of animals that are very large and the various types of obstacles they face in daily life. When Packy is bigger than the biggest elephant and cannot enter his home, he begins to realize the problems of being big.

Throughout his quest to feel comfortable with his growth, Packy is accompanied by his mosquito sidekick Zippy. His companion plays the role of a mentor and counselor throughout the various levels of Packy's adventures.

In part two the patient will learn about preparing and administering doses of growth hormone. First, the user will see how to mix a dose, then prepare a pen for injecting the hormone, and then actually see how an injection is performed. In the game aspect of this part the user will be challenged to mix and administer a dose seven times (Monday through Sunday) and provide accuracy results.

The third part of the game is a growth diary where the patient records and sees various graphics displaying his or her personal progress.

Playing this game is reassuring and helps children overcome growth disorders by emphasizing self-awareness and self-efficacy training, role-playing, competition, and strategies embedded in the video game. Analogous video game strategy is also used to treat anxiety and hyperactivity disorders, various types of phobias, as well as enuresis.

Diabetes

EXAMPLE 3

Figure 14:
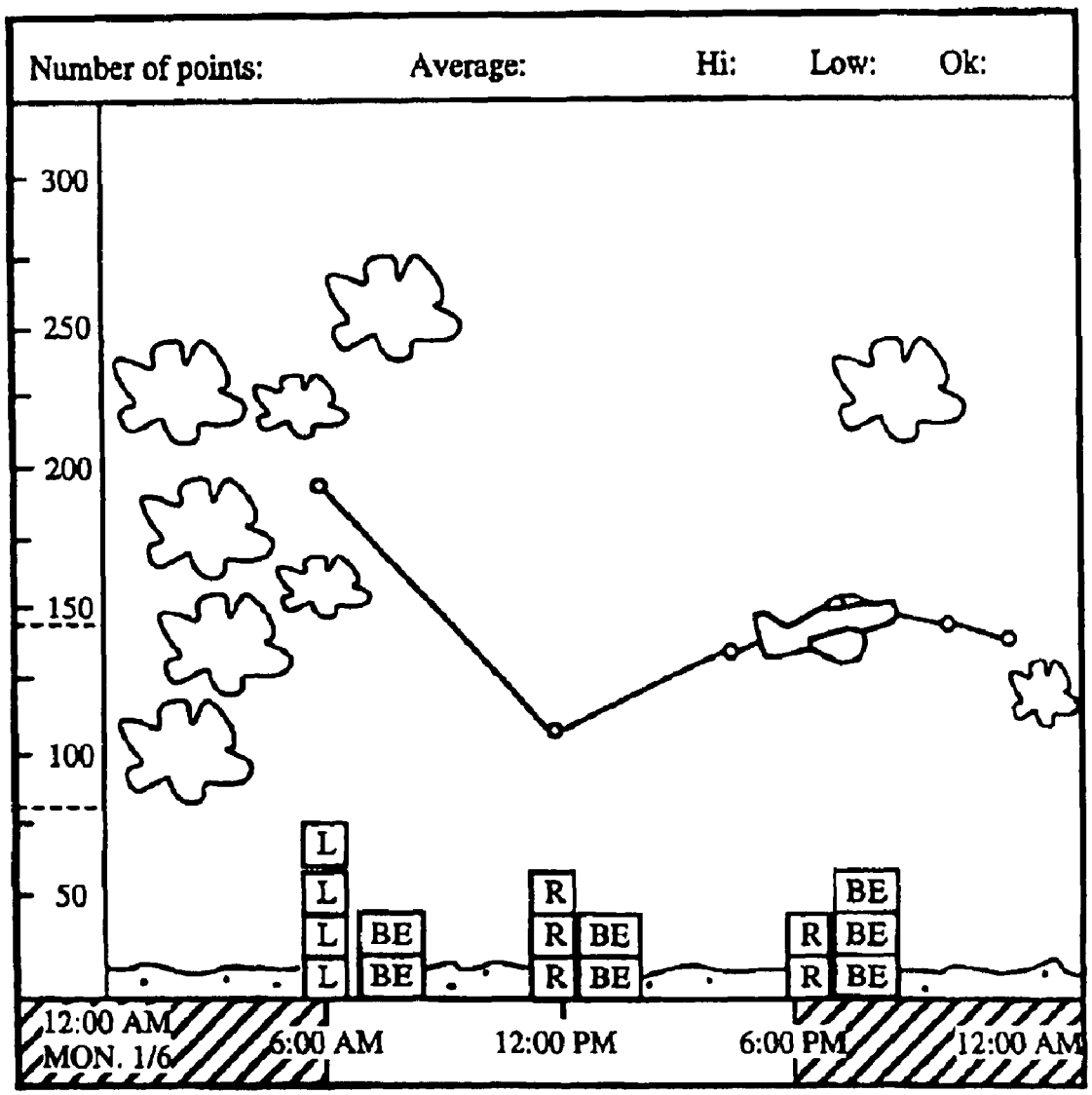
FIG. 14 is an exemplary screen of a video game for diabetes self-treatment according to the invention.
Figure 15:
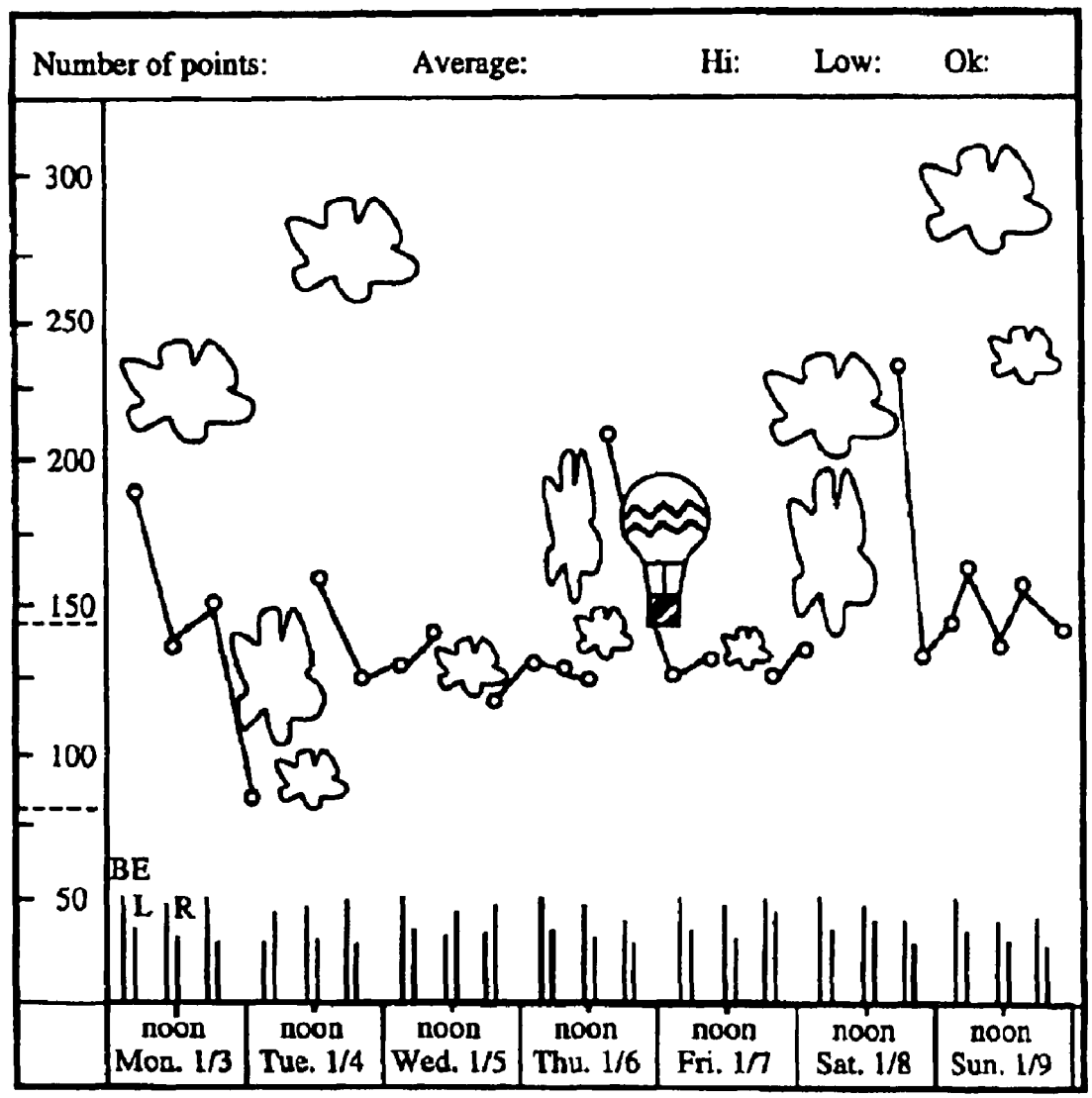
FIG. 15 is another exemplary screen for the video game FIG. 14.
Figure 20:
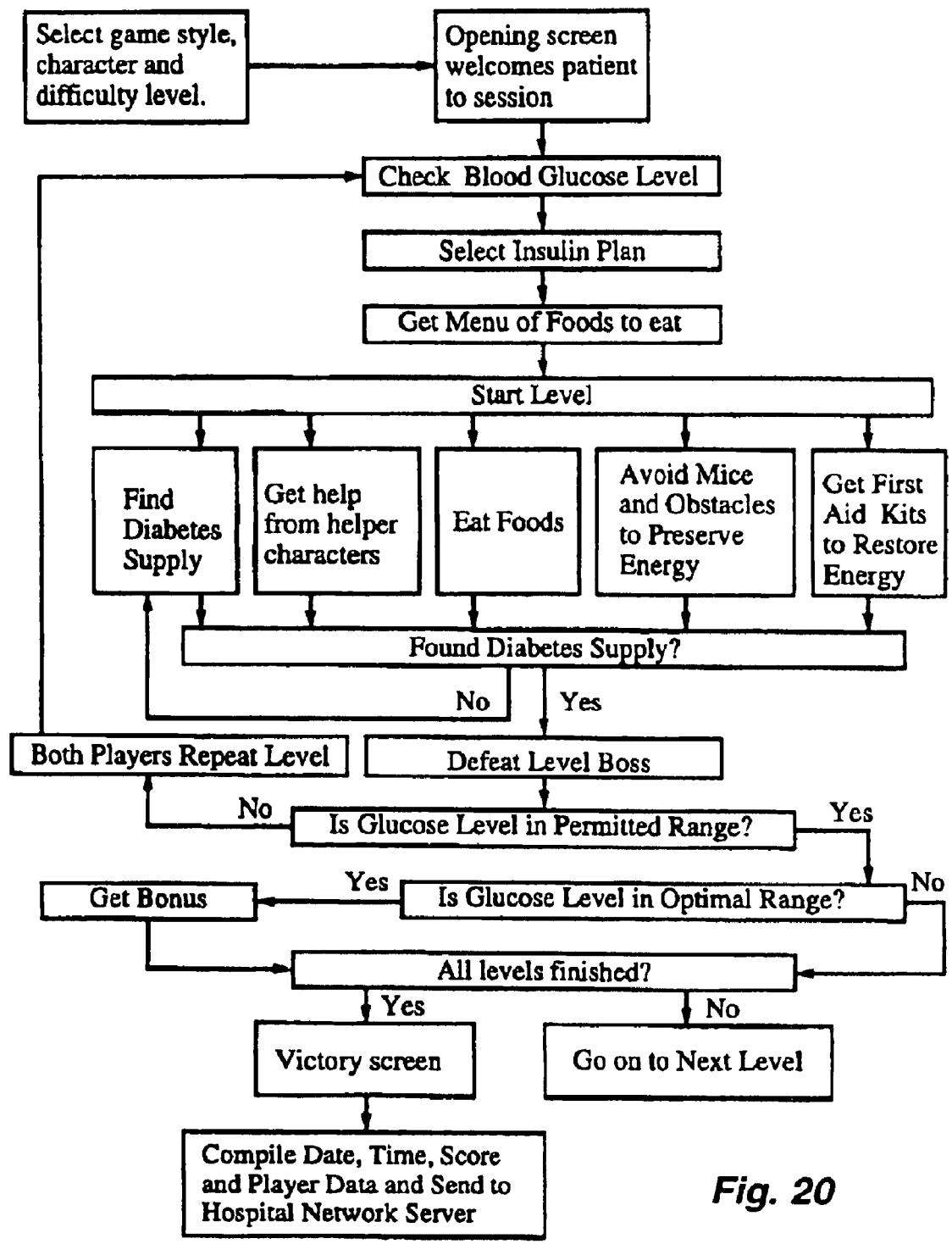

The patient is diagnosed with insulin-dependent diabetes. As treatment the physician prescribes insulin shots and a video game based on positive-reinforcement and self-management. In the video game the graphical game character is a pilot who has diabetes, just like the patient. The pilot needs to follow proper diet and exercise regimen to avoid crashing a plane or balloon which he is flying. The screens for the video game are shown in FIG. 14 and FIG. 15. The flowchart for this game is shown in FIG. 20. Eating wrong foods causes blood glucose level to increase and the plane or balloon starts gaining altitude uncontrollably. Eventually, above a certain threshold, the balloon or the plane spins out of control.

Figure 16:
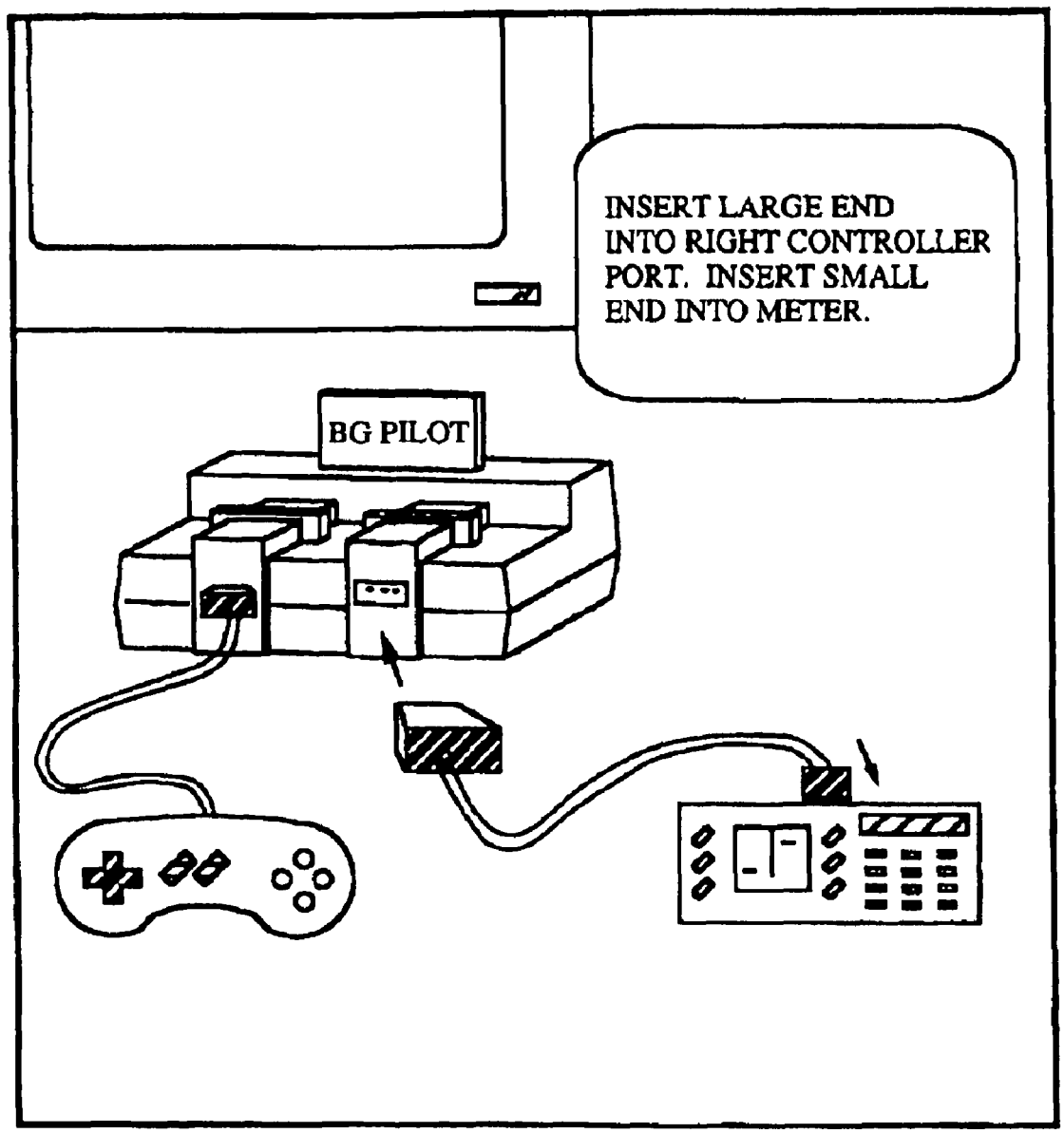
FIG. 16 is still another exemplary screen for the video game of FIG. 14.
Figure 17:
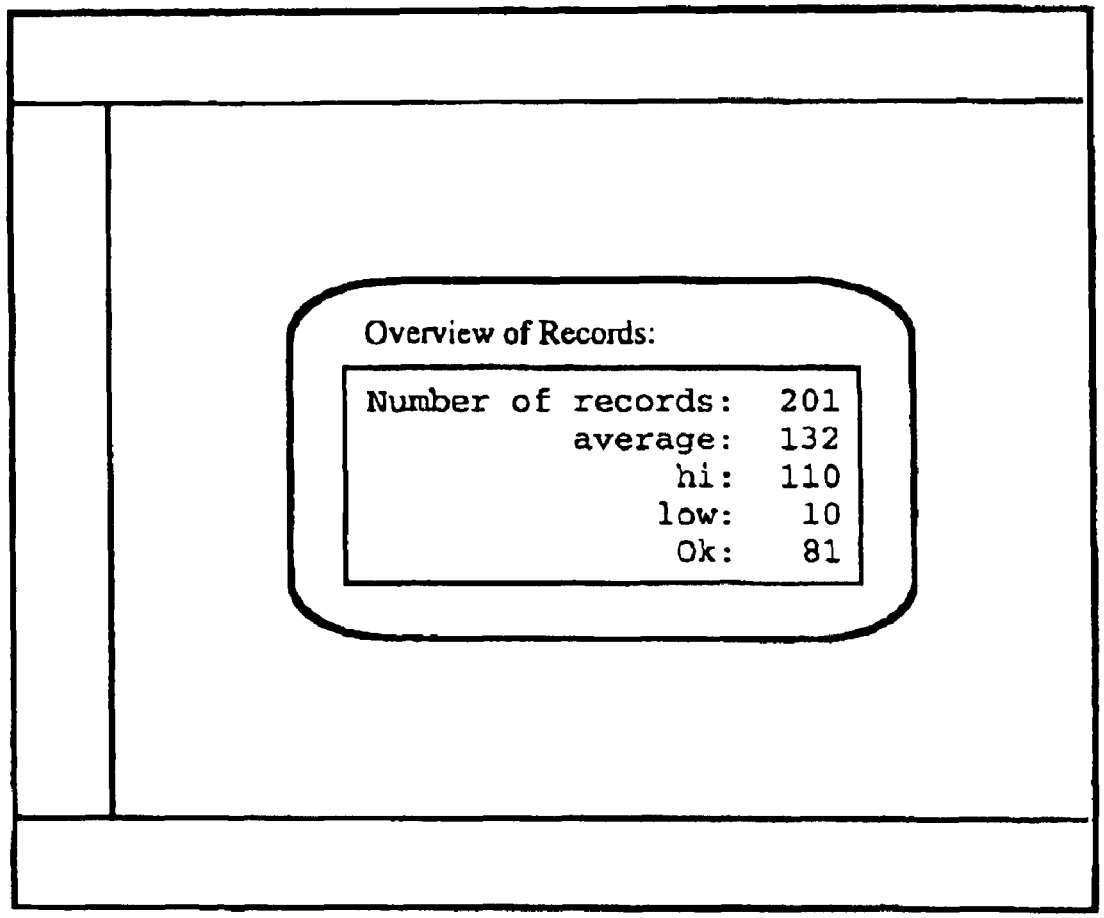
FIG. 17 is a screen indicating the blood glucose measurement results compiled for the video game of FIG. 14.

During the game the patient is requested to enter his own blood glucose level by using blood glucose meter 54. An exemplary set-up for doing this is shown in FIG. 16. The reading is used in the game and can also be transmitted to the hospital, as described in example 3. Also, the user can view his blood glucose readings in the form transmitted to the hospital and used in the game. An example of such reading for a number of measurement records is illustrated in FIG. 17.

If the user does not comply with the request for measuring and entering his blood glucose level the plane or balloon disappears behind clouds, representing uncertainty in blood glucose level. This is visualized by the clouds in FIGS. 14 and 15. The clouds obscure the pilot's vision and lead to collisions with objects in the plane's or balloon's path. Alternatively, if the blood glucose level drops below a minimum threshold, the plane or balloon crashes against the ground.

This positive reinforcement-based strategy, in which the blood glucose level is correlated to a game parameter, e.g., plane altitude, teaches the patient how to cope with his condition on a day-to-day basis while making blood glucose monitoring fun. It also produces higher treatment compliance rates, especially in children who need to learn early on about proper diabetes self-management.

Non-Insulin Dependent Diabetes Management

EXAMPLE 4

A video game treatment can be used for management of non-insulin dependent cases of diabetes (NIDDM). In such cases the video game is an interactive information resource, as well as a role-playing game. The game helps the patient, especially an adult patient, explore the topic of Staged Diabetes Management. The information is presented in hypertext format, allowing the patient to select a stage, read a brief overview of it, and select details to examine it in greater depth in desired. The game encourages active involvement in learning and provides opportunities to rehearse various health behaviors and see the consequences that result by observing what happens to a graphical game character who displays these behaviors.

The content of the game is based on the Staged Diabetes Management program, developed by the International Diabetes Center and Becton Dickinson & Company. The progressive set of stages ranges from least to most severe. For example, a patient in Stage I will learn to manage NIDDM through diet alone.

In the video game the user can configure the graphical game character in many ways. A checklist of chokes allows the patient to combine a variety of physical features and clothes, as well as specifics about the character's health status including weight, age, and medications taken.

The game character, and thus the patient, will make decisions in realistic settings such as restaurants and parties where rich foods are available. Also, an exercise plan will fit in with the character's busy schedule of family, community, and work commitments. This format provides the patient with a playful atmosphere in which choices which the patient faces in his or her own life can be rehearsed.

If blood glucose levels do not remain in the normal range in Stage I, then the patient is instructed by the graphical game character to advance to the next treatment steps, eventually arriving at the stage where the patient will be instructed to inject insulin to control blood glucose levels. The goal of the NIDDM game is to remain at Stage I.

Similar video games can help to deal with hemophilia, and other medical condition requiring the patient to be aware of his or her surroundings.

Asthma

EXAMPLE 5

A youngster diagnosed with asthma is given an asthma self-management game for hand-held unit 430. The graphical game character, a young dinosaur from the pre-historic town of Saurian, must cope with and manage his asthma. The game San character confronts common asthma triggers, while learning to recognize early warning signs of an oncoming asthmatic episode. Asthma management techniques including avoidance, relaxation, and medicinal inhalers are part of the daily routine for the young dinosaur who must return to his cave. The dinosaur runs, jumps, and shoots a squirt gun at oncoming triggers while conquering each level and mastering his condition. In addition to these inputs, the dinosaur requests the player to input the player's asthma condition by using physical parameter measuring device 454, which in this case is a respiratory flow meter. These data can then be transmitted to the physician as described above.

Playing the video game involving these real asthma triggers, relaxation techniques, etc., affects the mental state of the player to improve his own asthma management outside of video game sessions. This treatment based on role-playing and positive reinforcement makes the patient aware of the importance of prescribed drugs and teaches appropriate measures for dealing with the patient's condition in real life situations.

Eating Disorder

EXAMPLE 6

The physician determines that the patient suffers from an eating disorder causing the patient to gorge. The physician loads into the patient's microprocessor-based unit 410 or hand-held unit 430 a video game in which the graphical game character has to stay thin to survive. The game challenges confronting the game character include avoiding fatty foods to stay trim and eating a sufficient amount to combat dragons and surmount obstacles on his way. Doing this involves making choices about what food presented on the screen to eat, keep for later, or reject. Wrong food choices have immediate consequences in the graphical character's ability to survive. The game is scored according to the length of time the patient is capable of keeping his game character alive and obstacles the character overcomes.

The physician instructs the patient to play the game every time the patient feels an eating urge outside regular meal times. During a regular follow-up visit the doctor evaluates the patient's progress and checks the scores obtained in playing the video game. Based on the analysis of the sores the physician determines the severity of the problem and gets an insight into the patient's motivation to comply with the therapy. Sufficiently high scores reflect progress and readiness to proceed with the next treatment stage. At this point the physician may instruct the patient to play another video game designed for milder eating disorders or a game utilizing a different psychological approach, e.g., negative reinforcement or distraction.

Depression

EXAMPLE 7

A psychiatrist enrolls a patient in a series of home-based interactive video game sessions, which the patient accesses from his microprocessor-based unit 410 through hospital network 426. The video game is then transmitted from the hospital network server 428 to the patient's unit 410. The game involves interaction with a graphical game character resembling the Yoda character from the popular movie "Star Wars". Yoda acts as a counselor and mentor to the patient, preparing him for various trial episodes in the video game. Based on patient's scores in playing the video game sent, the physician reviews how the patient responds to video game counseling and prepares another game to be transmitted to the patient. This treatment method is part of an on-going therapy for mild to medium-severe depression. This approach is also used for schizophrenia and other purely psychological disorders.

SUMMARY, RAMIFICATIONS, AND SCOPE

The reader will thus see that I have presented a particularly simple method for treating medical conditions in human patients using a microprocessor-based video game. This method gives a better picture of the ailment through its standardized scoring procedure and makes the treatment much less costly by considerably reducing the number of therapy sessions with the physician or health care professional. In addition, video games emphasize superior treatment in the patient's own environment. This leads to self-help responses difficult to foster in therapy sessions. The patient recognizes the importance of medications and treatment regimens in an entertaining manner. Moreover, the patient participates actively in the treatment by following instructions embedded in the video game or even generating positive physiological responses due to stimuli presented in the video game.

The method of the invention also provides a treatment to which the patient can resort as the need arises. The intrinsic fun in playing video games ensures higher treatment compliance for all patients, and in particular children. The self-treatment instructions communicated by this method can be used to additionally induce patients to independently perform measurements of physical parameters associated with their medical condition.

Finally, the scoring of the video game provides an excellent standardized measure for evaluating treatment results and improving continued treatment. In carrying out the method the microprocessor-based system can be expanded to use any number of communications devices, monitoring set-ups, and other state-of-the-art medical equipment. Therefore, the scope of the invention should be determined, not be examples given, but by the appended claims and their legal equivalents.

The invention claimed is:

1. A method of diabetes management, comprising:
   (a) providing a communications unit remotely located from and in communication with a portable microprocessor-based unit;
   (b) advising a user to measure a blood glucose level by transmitting blood glucose level data into the portable microprocessor-based unit or the communications unit, or both;
   (c) running a program of instructions on the portable microprocessor-based unit or on the communications unit, or both, using data corresponding to the blood glucose level data, wherein said portable microprocessor-based unit comprises a multi-line display configured to present to said user (i) graphs of said blood glucose level data and (ii) a game-like presentation; and (d) advising said user to inject insulin according to an insulin plan;

(e) presenting to said user (a) said blood glucose level data and (b) information to educate said user regarding management of diabetes;

(f) receiving from said user responses confirming said blood glucose level has been measured; and (g) positively reinforcing compliance with a diabetes management plan by providing bonuses in said game-like presentation on said multi-line display in response to said blood glucose level being within an optimal range.

2. The method of claim 1, further comprising signal coupling a blood glucose meter with said portable microprocessor-based unit from which said blood glucose data are downloaded.

3. The method of claim 1, wherein (i) said program of instructions comprises a diabetes management plan and (ii) further comprising communicating a signal to said portable microprocessor-based unit to advance between steps of said diabetes management plan.

4. The method of claim 1, further comprising checking said blood glucose level as a result of running the program of instructions.

5. The method of claim 1, further comprising selecting said insulin plan as a result of running the program of instructions.

6. The method of claim 1, further comprising getting a menu of foods to eat as a result of running the program of instructions.

7. The method of claim 1, wherein said program of instructions are configured such that said advising said user to inject said insulin occurs when said blood glucose levels do not remain in a predetermined range.

8. One or more processor-readable storage devices having program code embodied therein for programming one or more processors to perform a method of diabetes management using a system including a communications unit remotely located from and in communication with a hand-held microprocessor-based unit, wherein the method comprises:

(a) advising a user to measure a glucose level;

(b) providing blood glucose level data based on the measured glucose level into the hand-held microprocessor-based unit;

(c) running a program of instructions on the hand-held microprocessor-based unit or on the communications unit, or both, using data corresponding to the blood glucose level data, wherein said hand-held microprocessor-based unit comprises a multi-line display configured to present to said user (i) graphs of said blood glucose level data and (ii) a game-like presentation; and (d) advising said user to inject insulin according to an insulin plan;

(e) presenting to said user (a) said blood glucose level data and (b) information to educate said user regarding management of diabetes;

(f) receiving from said user responses confirming said glucose level has been measured; and (g) positively reinforcing compliance with a diabetes management plan by providing bonuses in said game-like presentation on said multi-line display in response to said glucose level being within an optimal range.

9. The one or more processor-readable storage devices of claim 8, wherein the method further comprises signal coupling, a blood glucose meter with said hand-held microprocessor-based unit from which said blood glucose data are downloaded.

10. The one or more processor-readable storage devices of claim 8, wherein (i) the program of instructions comprises said diabetes management plan and (ii) the method further comprises communicating a signal to said hand-held microprocessor-based unit to advance between steps of said diabetes management plan.

11. The one or more processor-readable storage devices of claim 8, wherein the method further comprises checking said glucose level as a result of running the program of instructions.

12. The one or more processor-readable storage devices of claim 8, wherein the method further comprises selecting said insulin plan as a result of running the program of instructions.

13. The one or more processor-readable storage devices of claim 8, wherein the method further comprises getting a menu of foods to eat as a result of running the program of instructions.

14. The one or more processor-readable storage devices of claim 8, wherein said advising said user to inject said insulin occurs when said glucose levels do not remain in a predetermined range.

* * * * *